United States Patent
Miyamoto et al.

(10) Patent No.: US 9,476,836 B2
(45) Date of Patent: *Oct. 25, 2016

(54) NUCLEIC ACID DETECTION METHOD, AND DEVICE AND KIT FOR USE IN SAME

(71) Applicant: Kaneka Corporation, Osaka (JP)

(72) Inventors: Shigehiko Miyamoto, Takasago (JP); Jun Tomono, Takasago (JP); Koji Takahashi, Takasago (JP); Sotaro Sano, Takasago (JP); Takaaki Jikihara, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,811

(22) Filed: Jan. 20, 2016

(65) Prior Publication Data

US 2016/0209332 A1    Jul. 21, 2016

Related U.S. Application Data

(62) Division of application No. 14/002,886, filed as application No. PCT/JP2012/055601 on Mar. 5, 2012, now Pat. No. 9,273,174.

(30) Foreign Application Priority Data

Mar. 4, 2011   (JP) ................. 2011-048183
Aug. 9, 2011   (JP) ................. 2011-174105
Feb. 9, 2012   (JP) ................. 2012-026491

(51) Int. Cl.
*C12Q 1/68*   (2006.01)
*G01N 21/78*   (2006.01)
(Continued)

(52) U.S. Cl.
CPC ............. *G01N 21/78* (2013.01); *C08F 222/10* (2013.01); *C12Q 1/6806* (2013.01); *C12Q 1/6846* (2013.01); *C12Q 1/6848* (2013.01); *G01N 21/03* (2013.01); *Y10T 436/143333* (2015.01)

(58) Field of Classification Search
CPC .... C12Q 1/68; C12Q 1/6844; C12Q 1/6846; C12Q 1/686; C12Q 2547/10; C12Q 2547/101; C12Q 2563/103; C12Q 2563/173; C12Q 1/6806; C12Q 1/6848; Y10T 436/143333; G01N 21/03; G01N 21/77; G01N 21/78; G01N 33/583; C08F 222/10
USPC .......... 436/94, 164, 165, 166; 422/401, 405, 422/408, 425, 430, 82.05, 82.09, 547, 549, 422/550, 554, 558; 435/6.1, 6.12, 287.1, 435/287.2, 287.9, 288.1, 288.7
See application file for complete search history.

(56) References Cited

U.S. PATENT DOCUMENTS 5,049,490 A    9/1991   Sutherland et al.
6,645,758 B1   11/2003  Schnipelsky et al.
(Continued)

FOREIGN PATENT DOCUMENTS

CA   2745766 A1   9/2010
CN   1826171 A    8/2006
(Continued)

OTHER PUBLICATIONS

Loopamp Tanjun Herpes Virus (HSV-1/2) Kenshutsu Shiyaku Kit, Manual, Eiken Chemical Co., Ltd., 2010.
(Continued)

*Primary Examiner* — Maureen Wallenhorst
(74) *Attorney, Agent, or Firm* — Polsinelli PC

(57) ABSTRACT

The present invention aims to solve problems in the analysis of amplified nucleic acids, i.e., cost, workability, and contamination and pollution of samples. In the present invention, a sample containing a nucleic acid and a reagent for detecting the nucleic acid are mixed in a closed system. In this regard, the nucleic acid is amplified in the same closed system, and then mixed with the detecting reagent without opening the system. In order to carry out this method, for example, a device that includes the detecting reagent shielded by a coating material or the like is used.

13 Claims, 13 Drawing Sheets

(51) Int. Cl.
C08F 222/10 (2006.01)
G01N 21/03 (2006.01)

(56) References Cited

U.S. PATENT DOCUMENTS

| | | | |
|---|---|---|---|
| 9,097,718 B2* | 8/2015 | Miyamoto | ............ C12Q 1/6816 |
| 9,273,174 B2* | 3/2016 | Miyamoto | ............ C12Q 1/6846 |
| 2004/0142475 A1 | 7/2004 | Barman et al. | |
| 2004/0171016 A1 | 9/2004 | Tomita et al. | |
| 2005/0019944 A1 | 1/2005 | Qiao et al. | |
| 2005/0112770 A1 | 5/2005 | Nakamura et al. | |
| 2010/0330564 A1 | 12/2010 | Tomono | |
| 2011/0117549 A1 | 5/2011 | Miyamoto et al. | |

FOREIGN PATENT DOCUMENTS

| | | |
|---|---|---|
| CN | 101033484 A | 9/2007 |
| CN | 102356161 A | 2/2012 |
| EP | 0511712 A1 | 11/1992 |
| EP | 2410063 A1 | 1/2012 |
| EP | 2620508 A1 | 7/2013 |
| JP | 5237000 A | 9/1993 |
| JP | 9187275 A | 7/1997 |
| JP | 2002-345499 A | 12/2002 |
| JP | 2003-038161 A | 2/2003 |
| JP | 2003240780 A | 8/2003 |
| JP | 2009-201458 A | 9/2009 |
| JP | 4683811 B2 | 5/2011 |
| WO | WO-02/103053 A1 | 12/2002 |
| WO | WO-2005016515 A2 | 2/2005 |
| WO | WO-2010-106997 A1 | 9/2010 |

OTHER PUBLICATIONS

OptiGene-sha Toon Zofuku Keiko Sokutei Sochi Geniell Jizen Yoyaku Campaign, Catalog, Nippon Gene Co., Ltd., 2010.
International Preliminary Report on Patentability issued in PCT/JP2012/055601, date of issuance Sep. 10, 2013.
Yang et al., "Counterion-dye staining method for DNA in agarose gels using crystal violet and methyl orange", Electrophoresis 2001, 22, 855-859.
Gibson et al., "A Colorimetric Assay for Phosphate to Measure Amplicon Accumulation in Polymerase Chain Reaction", Analytical Biochemistry 254, 18-22 (1997).
Miyamoto et al., Analytical Biochemistry, vol. 473, Jan. 7, 2015, pp. 28-33.
Cong et al., "A visible dye-based staining method for DNA in polyacrylamide gels by ethyl violet", Analytical Biochemistry, vol. 402, No. 1, 2010, pp. 99-101, XP055099508.
Kong et al., "Fluorescent Sensor for Monitoring Structural Changes of G-Quadruplexes and Detection of Potassium Ion", Analytical Chemistry, vol. 81, No. 7, 2009, pp. 2678-2684, XP055099510.
Jin et al., "Usefulness of visible dyes for the staining of protein or DNA in electrophoresis", Electrophoresis, vol. 25, No. 15, 2004, pp. 2429-2438, XP055099512.
Miyamoto et al., "Pipette Tip-gata PCR Zofuku Hantei Tool D-Quick no Kaihatsu to sono Tokucho", JETI, Sep. 16, 2010, vol. 58, No. 10, pp. 60-63.
Partial translation of Funakoshi News, Feb. 1, 2011 Issue, p. 9.
Molecular Cloning Second Edition, vol. 1, 6.15, 1989, Gel Electrophoresis of DNA.
International Preliminary Report on Patentability issued in Application No. PCT/JP2011/071477 dated Apr. 16, 2013.

* cited by examiner

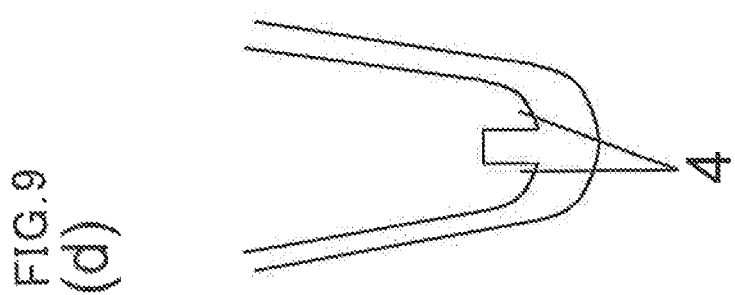
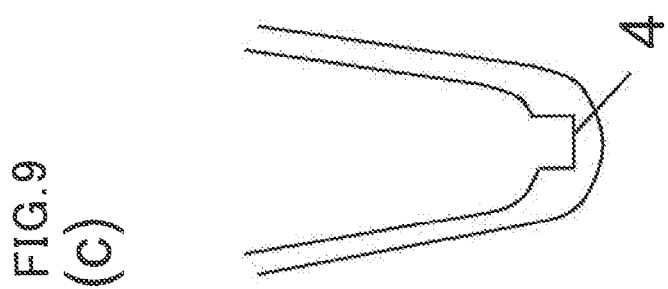
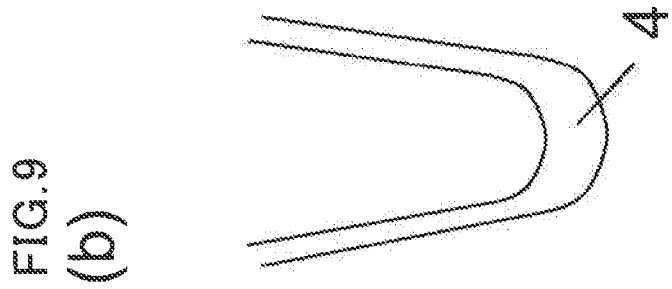
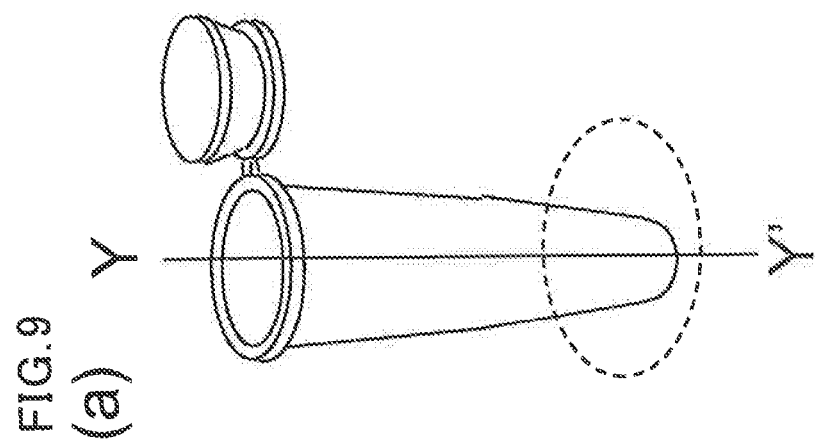
FIG. 9

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Primer F

<400> SEQUENCE: 1
ggaaacagct atgaccatga                                               20

<210> SEQ ID NO 2
<211> LENGTH: 19
<212> TYPE: DNA
<213> ORGANISM: Artificial
<220> FEATURE:
<223> OTHER INFORMATION: Primer R

<400> SEQUENCE: 2
ctatgcggca tcagagcag                                                19
```

NUCLEIC ACID DETECTION METHOD, AND DEVICE AND KIT FOR USE IN SAME

CROSS REFERENCE TO RELATED APPLICATIONS

This application is a Divisional of U.S. patent application Ser. No. 14/022,886 filed on Nov. 15, 2013, and now U.S. Pat. No. 9,273,174,which is a National Phase filing under 35 U.S.C. §371 of PCT/JP2012/055601 filed on Mar. 5, 2012; and this application claims priority to Application No. 2011-048183 filed in Japan on Mar. 4, 2011, Application No. 2011-174105 filed in Japan on Aug. 9, 2011 and Application No. 2012-026491 filed in Japan on Feb. 9, 2012; the entire contents of all are hereby incorporated by reference.

TECHNICAL FIELD

The present invention relates to a method of detecting a nucleic acid, and a device or kit for use in the method.

BACKGROUND ART

In clinical genetic testing of biological samples such as tissue, blood, saliva, and urine, and in gene analyses of food products and plants, methods for amplifying a nucleic acid, such as PCR (polymerase chain reaction) method and LAMP (loop-mediated isothermal amplification) method, are used to efficiently analyze the target nucleic acid. These methods are effective in detecting a small amount of target. However, after amplification, the resulting solution containing a nucleic acid needs to be collected and transferred to another operation for detection, requiring opening of the reaction container, which may lead to splashing of the sample containing a nucleic acid outside the container, and also lead to false positive results due to contamination with another reaction mixture. In addition, the detection of an amplified nucleic acid requires special devices and mature testing techniques. This is why the testing is not commonly performed in sampling sites such as clinical practice and bedside. As it stands now, the testing is only carried out in clinical laboratories and specialized research institutions.

A most commonly used method for detecting an amplified nucleic acid includes separating a solution with an amplified nucleic acid using agarose electrophoresis, followed by staining with a fluorescent intercalator and observation of a specific fluorescence (Non Patent Literature 1). The fluorescence detection, however, requires expensive compounds such as a primer or an intercalator and expensive apparatus such as excitation apparatus (e.g. UV illumination device) or gel imaging apparatus. Also, the electrophoresis of an amplified nucleic acid requires a prolonged phoresis process.

Of the methods for amplifying a nucleic acid, LAMP method is advantageous in that the reaction does not require temperature cycling and proceeds at a constant temperature, and that it provides a larger amount of amplified nucleic acid than PCR method does. In particular, known methods for detecting an amplified nucleic acid obtained by LAMP method, without using fluorescence, include: a method of detection of white turbidity which is based on the formation of an insoluble magnesium salt of pyrophosphoric acid that is a by-product of the reaction; and a method of detection of changes in magnesium concentration of the reaction mixture in the presence of a metallofluorescent indicator (Patent Literature 1, Non Patent Literature 2). In fact, these detection methods, however, still require devices such as a turbidimeter or a UV illumination device because it is impossible to visually identify the amplification with absolute accuracy.

Several attempts have been made to solve the disadvantages described above. For example, a device capable of carrying out amplification and detection of a nucleic acid in a single container has been reported (Patent Literature 2). This device, however, uses an expensive labeled primer and requires complex procedures including separately adding a detecting reagent. Also reported is a device in which a dried nucleic acid amplification reagent is preliminarily added to a container to enable simple operations as well as amplification of a nucleic acid in a closed system (Patent Literature 3). However, since the reaction container needs to be opened for detection, the operations through the completion of the detection are unable to be performed in the same closed system.

CITATION LIST

Patent Literature

Patent Literature 1: JP 4683811 B
Patent Literature 2: JP 2003-38161 A
Patent Literature 3: JP 2009-201458 A

Non Patent Literature

Non Patent Literature 1: Molecular Cloning second edition, vol. 1, 6.15 (1989)
Non Patent Literature 2: Nature Protocols, vol. 3, No. 5, pp. 877-882 (2008)

SUMMARY OF INVENTION

Technical Problem

The present invention aims to provide a method of detecting a nucleic acid which is capable of detecting a nucleic acid amplified by a nucleic acid amplification method, in the container under visible light immediately after the completion of the amplification. The present invention also aims to provide a detection device capable of performing steps from amplification of a nucleic acid to detection without opening a closed system of a container.

Solution to Problem

After keen examination, the present inventors have found that, by preliminarily charging a reaction container, which can form a closed system, or a lid thereof with a reagent for detecting a nucleic acid under visible light, the reagent is enabled to be dissolved in a solution containing an amplified nucleic acid without opening the reaction container; therefore, splashing and contamination of the sample can be prevented, and nucleic acid amplification can be easily and quickly detected under visible light. Thus, they have completed the present invention.

Specifically, the present invention relates to a method of detecting a nucleic acid, including the steps of: contacting a nucleic acid with a detecting reagent in a closed system; and observing a color change of at least one of the nucleic acid and the detecting reagent under visible light.

The method preferably further includes, prior to or after the contacting step, the step of amplifying the nucleic acid.

The detecting reagent is preferably in a solid form.

The detecting reagent preferably contains a leuco dye.

The leuco dye is preferably a triarylmethane dye.

The triarylmethane dye is preferably crystal violet or gentian violet.

The detecting reagent preferably contains at least one of a nucleophilic agent and a stabilizer.

The nucleophilic agent is preferably one or more nucleophilic agents selected from the group consisting of sodium borohydride, sodium cyanoborohydride, sodium bisulfite, sodium sulfite, sodium hydrosulfite, potassium pyrosulfite, sodium thiosulfate, glutathione, ascorbic acid, 2-mercaptoethanol, DL-dithiothreitol, 1-thioglycerol, cysteine, tributylphosphine, aminoethanethiol, and tris(2-carboxyethyl) phosphine.

The stabilizer is preferably one or more stabilizers selected from the group consisting of α-cyclodextrin, β-cyclodextrin, γ-cyclodextrin, and ascorbic acid.

The nucleic acid is preferably amplified by LAMP method. In the LAMP method, a pyrophosphatase is preferably used. The pyrophosphatase is preferably a heat resistant pyrophosphatase.

The present invention also relates to a device or kit for detecting a nucleic acid, including a carrier carrying a detecting reagent, and a lid and/or a reaction container which are to be provided with the carrier.

The lid and/or reaction container preferably further carries a nucleic acid amplification reagent.

The detecting reagent is preferably shielded from a nucleic acid by a coating material.

The present invention also relates to an apparatus, including the device or kit for detecting a nucleic acid.

Advantageous Effects of Invention

The present invention enables to easily perform steps from amplification of a nucleic acid to detection under visible light, in the same closed system so that splashing and contamination of the sample can be prevented.

BRIEF DESCRIPTION OF DRAWINGS

FIG. 2(b) is a schematic view illustrating the device shown in FIG. 2 (a) when viewed from the opening side. FIG. 2(c) is a schematic view illustrating the device shown in FIG. 2(a) cut along the line X-X' shown in FIG. 2(b) when viewed from the lateral side with the opening up.

FIG. 9(a) is a schematic view of a detection device (reaction container form I). FIG. 9(b) is a schematic view illustrating a reagent carrier of the device shown in FIG. 9(a) cut along the line Y-Y' shown in FIG. 9(a) when viewed from the lateral side. FIGS. 9(c) and 9(d) are schematic views illustrating a reagent carrier of a subtype (reaction container form II) of the detection device shown in FIG. 9(a) when viewed from the lateral side, as is the case in FIG. 9(b).

DESCRIPTION OF EMBODIMENTS

Figure 1A:
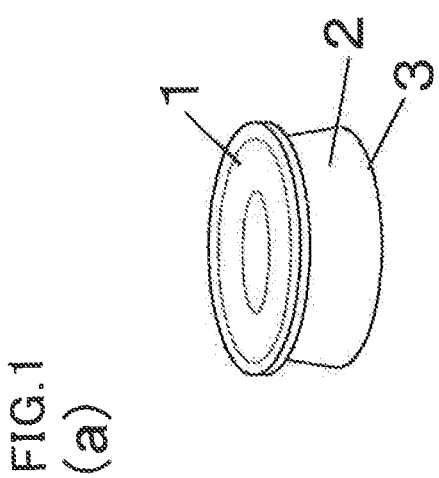
FIG. 1(a) is a schematic view of a detection device (lid form, projecting type I).

In the following, the present invention is described in detail.

The present invention relates to a method of detecting a nucleic acid, including the steps of: contacting a nucleic acid with a detecting reagent in a closed system; and observing a color change(s) of the nucleic acid and/or the detecting reagent under visible light.

Nucleic acids applicable in the present invention include amplified nucleic acids obtained by nucleic acid amplification methods, double-stranded DNAs, double-stranded RNAs, DNA-RNA hybrid chains, and double-stranded artificial nucleic acids such as PNA. The target nucleic acid may be a single-stranded nucleic acid. This is because when, for example, single-stranded RNA is reverse-transcribed into DNA by reverse transcriptase, and a double-stranded nucleic acid is amplified using the DNA as a template, then the RNA can be indirectly detected.

The nucleic acid may be contained in a sample. Examples of the sample include: amplified nucleic acids obtained by nucleic acid amplification methods; biological samples containing a nucleic acid; extracts from, for example, microorganisms, animal cells, or plant cells; and extracts from food products. The nucleic acid may be DNA extracted from a biological sample or plasmid DNA.

The method for contacting a nucleic acid with a detecting reagent is not limited as long as it causes the nucleic acid and/or the detecting reagent to exhibit a color change. For example, a solution containing a nucleic acid may be mixed with a liquid detecting reagent. Or alternatively, a solution containing a nucleic acid may be brought into contact with a solid detecting reagent.

The "closed system" herein means a consistently closed system that does not allow addition or removal of the sample containing a nucleic acid between the steps of amplifying and detecting a nucleic acid. However, the system is not required to be completely airtight. For example, if there is no leakage of the nucleic acid and detecting reagent after turning the container upside down or like operations to contact the nucleic acid with the detecting reagent in the container, such a system falls under the closed system in the present invention. The contacting of a nucleic acid with a detecting reagent in a closed system can prevent false detection due to mixing of different nucleic acids, and contamination caused by splashing of the nucleic acid. In addition, in the case where a step of amplifying a nucleic acid is performed prior to or after the contacting step, performing all the amplification step, contacting step, and step of observation under visible light in a closed system can prevent false detection and contamination and enable rapid observation under visible light, even when a highly-sensitive amplification method is used.

In the step of observing a color change (s) of the nucleic acid and/or the detecting reagent under visible light, a substance produced by the contact of the nucleic acid and detecting reagent is observed under visible light such as common lighting in experimental laboratories, without irradiation with light other than visible light such as ultraviolet light, to identify the presence of the nucleic acid. The use of visible light allows simple observation as it requires no special device, unlike in the case of ultraviolet light irradiation.

The color change can be visually observed under visible light. A change in color caused by binding of a dye to a nucleic acid and a change in color caused by the dye not bound to the nucleic acid can be visually observed under visible light, so that the presence or absence of the nucleic acid can be identified based on the presence or absence of the color change of the dye.

The change in color may, for example, be a change in the kind of color under visible light (visible light wavelength) or a change in the shade of color (reflectance), but is not limited thereto as long as it can be observed under visible light. Examples of the change in the kind of color include a change from purple-red to light blue and a change from yellow to purple-red.

The observation of the color change under visible light can also be performed by measuring absorbance of the sample solution in the visible light range. Whether the observation is performed visually or by absorbance measurement, the wavelength of light to irradiate the nucleic acid and detecting reagent and the wavelength of light for observation are both in the visible light range. The wavelength of visible light is preferably 380 to 800 nm, more preferably 400 to 780 nm, and further preferably 450 to 750 nm. The measurement wavelength may be appropriately set within the visible light range according to the dye to be used. Moreover, the nucleic acid concentration in the sample can be determined by absorbance measurement.

Alternatively, if an insoluble precipitate of the dye and nucleic acid is formed, the amount of the nucleic acid can be determined from the amount of the precipitate collected using a filter or a membrane or by centrifugation.

In the present invention, a colored sample liquid obtained through the detection of a nucleic acid may be directly used in other molecular biological operations. Examples of the molecular biological operations include enzyme reactions such as a restriction enzyme reaction, sequencing reaction and PCR, and confirmation by electrophoresis.

Preferably, the method of the present invention includes, prior to or after the step of contacting a nucleic acid with a detecting reagent, the step of amplifying the nucleic acid. The method for amplifying the nucleic acid is not particularly limited as long as it is capable of amplifying a nucleic acid sequence, as typified by PCR method. Examples of the method of amplifying a nucleic acid sequence other than PCR method include, but not limited to, known methods such as LCR (Ligase Chain Reaction) method, SDA (Strand Displacement Amplification) method, RCA (Rolling Circle Amplification) method, CPT (Cycling Probe Technology) method, Q-Beta Replicase Amplification Technology method, ICAN (Isothermal and Chimeric primer-initiated Amplification of Nucleic Acids) method, LAMP (Loop-Mediated-Isothermal Amplification of DNA) method, NASBA (Nucleic acid Sequence-based Amplification) method, and TMA (Transcription mediated amplification) method.

In the Q-Beta Replicase Amplification Technology method, RCA method, NASBA method, SDA method, TMA method, LAMP method, ICAN method, and the like, the amplification reaction is performed at a constant temperature. In the other methods including the PCR method and LCR method, the amplification reaction is performed by thermal cycling.

Moreover, if RNA is reverse-transcribed into DNA by reverse transcriptase, and a double-stranded nucleic acid is amplified using the DNA as a template, then the RNA can be indirectly detected.

The use of the LAMP method for amplifying the nucleic acid is advantageous in that the method is simple because the reaction does not require thermal cycling, and in that it provides a large amount of amplified nucleic acid. In the LAMP method, the amplification reaction may be performed in the presence of a pyrophosphatase to increase reaction efficiency. Examples of the pyrophosphatase include pyrophosphatases, which degrade pyrophosphate into monophosphate, and ATP-sulfurylases, which bind pyrophosphate to adenosine 5'-phosphosulfate. In the present invention, heat resistant pyrophosphatases are particularly preferred.

The detecting reagent herein means a reagent for detecting a nucleic acid and contains a dye that binds to a nucleic acid. The detecting reagent may further contain a substance that preferentially reacts with a dye bound to a single-stranded nucleic acid and the dye not bound to any nucleic acid.

The dye herein means a substance which absorbs visible light to exhibit a color change. The dye that binds to a nucleic acid is not particularly limited as long as it is capable of binding to a nucleic acid. Examples thereof include triphenylmethane dyes, thiazine dyes, oxazine dyes, azine dyes, phenazine dyes, xanthene dyes, phenanthridium dyes, azo dyes, lactone dyes, sultone dyes, indigoid dyes, cyanine dyes, oxonol dyes, styryl dyes, porphyrin dyes, thioxanthene dyes, squarylium dyes, croconium dyes, azulenium dyes, ditiol metal salt dyes, naphtoquinone dyes, anthraquinone dyes, indophenol dyes, coumarine dyes, keto-coumarin dyes, pyrylium dyes, thiopyrylium dyes, thiazole dyes, quinoline dyes, benzophenone dyes, thiobenzophenone dyes, and mixtures thereof.

Preferred are triphenylmethane dyes, thiazine dyes, oxazine dyes, azine dyes, phenazine dyes, xanthene dyes, phenanthridium dyes, azo dyes, indigoid dyes, lactone dyes, sultone dyes, and mixtures thereof.

Examples of the triphenylmethane dyes include methyl green, malachite green, crystal violet, pararosaniline, gentian violet B, gentian violet R, night blue, victoria blue B, victoria blue R, victoria blue 4R, victoria blue BO, rosolic acid, fuchsin, acid fuchsin, basic fuchsin, new fuchsin, bromothymol blue, bromocresol green phenolphthalein, bromophenol blue, patent blue violet, phenol red, pigment blue 1, pigment violet 3, benzyl violet, pentamethylpararosaniline, fast green FCF, ethyl violet, green S, rosaniline, acid blue 7, azure blue G, solochrome cyanine R, acid blue 147, light green SF yellow, light green SF, ethyl green, aniline blue, methyl violet, and chrome violet CG.

Examples of the thiazine dyes include toluidine blue O, methylene blue, thionine, azure A, and thiol C.

Examples of the oxazine dyes include brilliant cresyl blue, nile blue, gallocyanine, and basic blue 3.

Examples of the azine dyes include aniline black and acetylene black.

Examples of the phenazine dyes include neutral red, janus green B, basic red 2, and safranine B.

Examples of the xanthene dyes include fluorescein, rhodamine, and pyronin Y.

Examples of the phenantridium dyes include ethidium bromide.

Examples of the azo dyes include bismarck brown, new coccin, and basic red 29. Examples of the indigoid dyes include indigo carmine.

The amount of the detecting reagent to be added to the sample is not particularly limited as long as the color change can be observed under visible light. The amount is typically 10% or less, preferably 1% or less, and more preferably 0.1% or less.

Of the dyes, preferred are those having the property of binding to a nucleic acid to change its color tone and also having the property of undergoing a change in structure to change its color tone, but those having only one of the properties may be used. These dyes may be used alone, or two or more of them may be used in combination.

Examples of the dye having the property of binding to a nucleic acid to change its color tone include toluidine blue O, methyl green, brilliant cresyl blue, gentian violet B, and victoria blue B. Specifically, toluidine blue O is navy blue in the absence of a double-stranded nucleic acid, and turns light blue when bound to a nucleic acid. Also, methyl green is light blue in the absence of a nucleic acid, and turns blue green when bound to a nucleic acid. Brilliant cresyl blue is dark blue in the absence of a nucleic acid, and turns blue green when bound to a nucleic acid.

Examples of the dye that undergoes a change in structure to change its color tone include pH-responsive dyes and redox-responsive dyes which change their color tone depending on the protonation state or the redox state. Examples of the change in structure include a change in conjugate structure, introduction or conversion of a substituent, and a change in protonation state.

The pH-responsive dye herein means a dye that changes its color tone depending on the hydrogen ion concentration (pH) in a solution, as typified by pH indicators. Examples thereof include those which turn purple-red from colorless (e.g. phenolphthalein) or turn orange from red (e.g. methyl orange) when the solution is changed from acidic to alkaline.

The redox-responsive dye herein means a dye that changes its color tone depending on whether it is in an oxidized state or a reduced state, such as, for example, dyes used in acid-base indicators or redox indicators. For example, methylene blue and methyl green are blue when they are oxidized, and turn colorless when reduced. Toluidine blue O, on the other hand, is blue when it is oxidized, and turns purple-red when reduced.

In the case of using a dye having the property of undergoing a change in structure to change its color tone, the contrast between color tones resulting from the presence and absence of a nucleic acid can be enhanced by adding a step of adding a substance that preferentially reacts with a dye bound to a single-stranded nucleic acid and the dye not bound to any nucleic acid, compared to the dye bound to a double-stranded nucleic acid. This enhancement facilitates the detection under visible light. More specifically, when color tones other than that derived from a dye bound to a double-stranded nucleic acid are changed or decolorized to colorless, the contrast between color tones resulting from the presence and absence of the double-stranded nucleic acid can then be enhanced. The step enables the identification of amplification of a double-stranded nucleic acid even in the case of using a dye that binds to a double-stranded nucleic acid but provides a slight change or no change in color tone after the binding to the double-stranded nucleic acid as long as the dye is pH responsive or redox-responsive.

For example, the change in color tone of methyl green when bound to a double-stranded nucleic acid is difficult to visually observe. However, the addition of a substance that preferentially reacts with methyl green bound to a single-stranded nucleic acid and methyl green not bound to any nucleic acid decolorizes light blue derived from methyl green not bound to a double-stranded nucleic acid. This method facilitates the identification of the presence or absence of a nucleic acid as follows. If the sample is colored, it indicates the presence of a double-stranded nucleic acid, whereas if the sample is colorless, it indicates the absence of a double-stranded nucleic acid.

As another example, toluidine blue O changes from navy blue to blue when bound to a double-stranded nucleic acid. If a substance that preferentially reacts with toluidine blue O bound to a single-stranded nucleic acid and toluidine blue O not bound to any nucleic acid is further added, then navy blue derived from toluidine blue not bound to a double-stranded nucleic acid is changed to purple-red. This can facilitate the identification of the presence or absence of a nucleic acid as follows. If the sample is blue, it indicates the presence of a double-stranded nucleic acid, whereas if the sample is purple-red, it indicates the absence of a double-stranded nucleic acid.

As still another example, the change in color tone of gentian violet B when bound to a double-stranded nucleic acid is difficult to visually observe. However, the addition of a substance that preferentially reacts with gentian violet B bound to a single-stranded nucleic acid and gentian violet B not bound to any nucleic acid decolorizes violet derived from gentian violet B not bound to a double-stranded nucleic acid. This can facilitate the identification of the presence or absence of a nucleic acid as follows. If the sample is violet, then it indicates the presence of a double-stranded nucleic acid, whereas if the sample is colorless, it indicates the absence of a double-stranded nucleic acid.

As still another example, the change in color tone of victoria blue B when bound to a double-stranded nucleic acid is difficult to visually observe in a neutral solution. However, in a higher-than-neutral or alkaline pH environment, blue derived from victoria blue B not bound to a double-stranded nucleic acid is changed to pale red. This can facilitate the identification of the presence or absence of a nucleic acid as follows. If the sample is blue, it indicates the presence of a double-stranded nucleic acid, whereas if the sample is pale red, it indicates the absence of a double-stranded nucleic acid.

The dye to be used for enhancing the contrast between color tones in this step is not particularly limited. The dye may be a dye that changes from colored to colorless or from colorless to colored depending on a change in its structure when not bound to a double-stranded nucleic acid, or a dye that changes its color tone, for example, from blue to red.

Preferred among these is a dye that changes from colored to colorless or from colorless to colored depending on a change in its structure because it enables easy identification of the presence or absence of a nucleic acid.

The substance that preferentially reacts with a dye bound to a single-stranded nucleic acid and the dye not bound to any nucleic acid is preferably one which changes the structure of the dye to cause a color change. Examples thereof include nucleophilic agents, oxidizing agents, reducing agents, acids, bases, and pH buffers.

In the case of using a redox-responsive dye, an oxidizing agent, a reducing agent, or the like may be used as the substance that preferentially reacts with a dye bound to a single-stranded nucleic acid and the dye not bound to any nucleic acid to change the color tone.

The oxidizing agent is not particularly limited as long as it has an oxidative effect, and examples thereof include hydrogen peroxide, potassium permanganate, potassium chlorate, potassium dichromate, sodium bromate, potassium bromate, halogens, concentrated sulfuric acid, nitric acid, sodium hypochlorite, chlorine dioxide, chloramine, osmium tetroxide, dimethyl sulfoxide, and meta-chloroperbenzoic acid.

Similarly, the reducing agent is not particularly limited as long as it has a reducing effect, and examples thereof include sodium borohydride, sodium cyanoborohydride, sodium hydrogen sulfite, sodium sulfite, sodium hydrosulfite, potassium pyrosulfite, sodium thiosulfate, glutathione, ascorbic acid, 2-mercaptoethanol, DL-dithiothreitol, 1-thioglycerol, cysteine, tributylphosphine, aminoethanethiol, tris(2-carboxyethyl)phosphine, and derivatives thereof.

Also in the case of using a pH-responsive dye, an acid or a base may be used as the substance that preferentially reacts with a dye bound to a single-stranded nucleic acid and the dye not bound to any nucleic acid to change the color tone.

Suitable examples of the acid include, but not limited to, mineral acids such as hydrochloric acid, sulfuric acid, and nitric acid, and organic acids such as acetic acid, formic acid, oxalic acid, citric acid, and lactic acid. Preferred are hydrochloric acid, sulfuric acid, acetic acid, and citric acid, and particularly preferred are hydrochloric acid and acetic acid.

Suitable examples of the base include, but not limited to, sodium hydroxide, potassium hydroxide, sodium bicarbonate, potassium carbonate, ammonia, and triethylamine. Preferred are sodium hydroxide, potassium hydroxide, and sodium bicarbonate, and particularly preferred are sodium hydroxide and sodium bicarbonate.

Examples of the nucleophilic agent include sulfite ion-containing substances such as sodium sulfite, bisulfite ion-containing substances such as sodium bisulfite, nitrate ion-containing substances such as sodium nitrate, nitrite ion-containing substances such as sodium nitrite, cyanide ion-containing substances such as sodium cyanide, halide ions, nitrogen nucleophilic agents, sulfur nucleophilic agents, alkali metal alkoxides, alkali metal hydroxides, and hydride nucleophilic agents.

Examples of the "halide ions" include fluoride ion, chloride ion, bromide ion, and iodide ion.

Examples of the "nitrogen nucleophilic agents" include amine nucleophilic agents such as ammonia, methylamine, n-propylamine, dimethylamine, benzylamine, N-methylbenzylamine, aniline, n-heptylamine, 1-aminodecane, and 1,3-diaminopropane; amide nucleophilic agents such as acetylamide; imide nucleophilic agents such as diacetylimide, diformylimide, phthalimide, and metal salts of phthalimide; and sulfonylamide nucleophilic agent such as benzenesulfonylamide, p-nitrobenzenesulfonylamide, o-nitrobenzenesulfonylamide, m-nitrobenzenesulfonylamide, and p-toluenesulfonylamide.

Examples of the "sulfur nucleophilic agents" include thiol, disulfide, and thiourea.

Examples of the "alkali metal alkoxydes" include sodium mehoxide, sodium ethoxide, and potassium tert-butoxide.

Examples of the "alkali metal hydroxides" include sodium hydroxide and potassium hydroxide.

The "hydride nucleophilic agent" means a reagent capable of supplying hydrogen to serve as a nucleophilic agent. Examples thereof include sodium triacetoxyborohydride, sodium borohydride, lithium tetrahydroborate, pyridine borane complex, tetrahydrofuran borane complex, 2-picoline borane complex, dimethyl sulfide-borane complex, sodium cyanoborohydride, lithium triethylborohydride, lithium aluminum hydride, Red-Al [sodium bis (2-methoxyethoxy)aluminum hydride], L-Selectride [lithium tri(sec-butyl)borohydride], K-Selectride [potassium tri(sec-butyl) borohydride], and DIBAL-H (diisobutylaluminium hydride).

Specifically, the nucleophilic agent is preferably at least one nucleophilic agent selected from the group consisting of sodium borohydride, sodium cyanoborohydride, sodium bisulfite, sodium sulfite, sodium hydrosulfite, potassium pyrosulfite, sodium thiosulfate, glutathione, ascorbic acid, 2-mercaptoethanol, DL-dithiothreitol, 1-thioglycerol, cysteine, tributylphosphine, aminoethanethiol, and tris(2-carboxyethyl)phosphine.

Also, a pH buffer may be used as the substance that preferentially reacts with a dye bound to a single-stranded nucleic acid and the dye not bound to any nucleic acid to change the color tone, in order to cause a change in color tone by a change in pH of a sample.

The pH buffer is not particularly limited as long as it changes the pH of a sample, and suitable examples thereof include Good buffers such as MES, Bis-Tris, ADA, PIPES, ACES, MOPSO, BES, MOPS, TES, HEPES, DIPSO, TAPSO, POPSO, HEPPSO, EPPS, Tricine, Tris, Bicine, TAPS, CHES, CAPSO, and CAPS, glycine, phosphoric acid, phthalic acid, citric acid, barbituric acid, succinic acid, citric acid, acetic acid, and carbonic acid.

Specifically, the amount of the substance that preferentially reacts with a dye bound to a single-stranded nucleic acid and the dye not bound to any nucleic acid to change the color tone cannot be uniformly defined as it depends on the kind of dye and the kind of the substance. An ordinary person skilled in the art can experimentally determine the amount that most facilitates the observation under visible light. For example, the amount of the substance reacting with a dye is preferably 1000 molar equivalents or less, and more preferably 100 molar equivalents or less, relative to the amount of the dye.

In the detection of a nucleic acid amplification product according to the method of the present invention, a dye and a substance that preferentially reacts with the dye bound to a single-stranded nucleic acid and the dye not bound to any nucleic acid may be added to enhance the color contrast. Also, in order to enhance the color contrast, the amplification reaction may be performed in the presence of a dye added in advance, and then a substance that preferentially reacts with the dye bound to a single-stranded nucleic acid and the dye not bound to any nucleic acid may be added to the reaction mixture after the reaction in a closed space using the detection device of the present invention.

The substances that preferentially react with a dye bound to a single-stranded nucleic acid and the dye not bound to any nucleic acid may be used alone, or two or more of them may be used in combination. Moreover, if a sample with a nucleic acid contains, from the start, a substance that preferentially reacts with a dye bound to a single-stranded nucleic acid and the dye not bound to any nucleic acid, the nucleic acid can then be detected by simply performing the step of reaction with the dye.

The dye and the substance that preferentially reacts with the dye bound to a single-stranded nucleic acid and the dye not bound to any nucleic acid may be mixed together before use.

The detecting reagent may contain a leuco dye. The leuco dye means a colorless or light colored dye which changes its structure by reacting with a color developer or receiving a physical stimulus such as light to exhibit a color change. Known color developers for leuco dyes include oxidizing agents and alcohols, but in the detection method of the present invention, a multi-stranded nucleic acid serves as the color developer.

The leuco dye is not particularly limited as long as it has the property of interacting with a nucleic acid to substantially provide a color change. Examples thereof include triarylmethane dyes, xanthene dyes, quinolline dyes, phenothiazine dyes, phenoxazine dyes, and mixtures thereof.

Leuco dyes usable for the detection of a nucleic acid in the present invention include triarylmethane dyes phenothiazine dyes, and phenoxazine dyes. Preferred among these are triarylmethane dyes.

Specific examples of the triarylmethane dyes include methyl green, malachite green, crystal violet, pararosaniline, gentian violet B, gentian violet R, night blue, victoria blue B, victoria blue R, and the quinoline dye 4-(p-dimethyl-amino styryl) quinoline. Preferred among these are leuco derivatives of crystal violet and gentian violet B. Here, if gentian violet is used as the leuco dye, only non-conjugated gentian violet falls into the leuco dye in the present invention. Conjugated gentian violet, which contacts a nucleic acid separately from a nucleophilic agent, does not fall into the leuco dye.

Specific examples of the phenothiazine dyes include phenothiazine and benzoyl leuco methylene blue.

Specific examples of the phenoxazines dyes include phenoxazine and other leuco derivatives.

In the present invention, a colored dye may be converted to a leuco dye. The colored dye means a dye in a colored state obtained by contacting a leuco dye with a color developer. For example, a colored triarylmethane dye can be converted to a leuco dye via reaction with a nucleophilic agent. In this case, even a single triarylmethane dye can provide leuco dyes having different structures if different nucleophilic agents are used.

In detecting an amplified nucleic acid using a leuco dye, the leuco dye is preferably added to a reaction mixture before the nucleic acid amplification reaction, but may be mixed with the reaction mixture after the nucleic acid amplification reaction.

To a sample for nucleic acid amplification may be added a leuco dye alone or a mixture of a leuco dye and a stabilizer. The stabilizer means a compound that prevents a leuco dye from becoming colored. Examples thereof include amines, thiol compounds, clathrate compounds such as α-cyclodextrin, β-cyclodextrin, and γ-cyclodextrin, and antioxidants such as ascorbic acid, but the stabilizer is not limited thereto as long as it can prevent coloring. The stabilizers may be added alone, or two or more stabilizers may be added in combination.

Moreover, instead of directly adding a leuco dye to a multi-stranded nucleic acid, a colored dye may be converted to a leuco dye through treatment with a nucleophilic agent or the like, and then added to the sample. Or alternatively, a mixture of a colored dye and a nucleophilic agent may be added to the sample. For example, crystal violet is mixed with sodium sulfite and thereby converted to a leuco dye, and the resultant mixture can be used for the detection of a multi-stranded nucleic acid. Use of a mixture of a colored dye and an agent that converts a colored form to a leuco form (e.g. a nucleophilic agent) is effective especially when the leuco dye is unstable and difficult to isolate.

The detecting reagent may be in a solid form. The detecting reagent in a solid form means that the reagent to be used for the detection is solidified by removing moisture from the reagent by a hot air, vacuum, steam, barrel, spin, suction or like technique. Such a detecting reagent may be advantageous due to its good workability. This is because that a liquid detecting reagent may lead to difficulty in shielding and the like.

The detecting reagent may be shielded from a nucleic acid by a coating material. The phrase "shielded from a nucleic acid" means that the detecting reagent is temporarily shielded from a sample containing a nucleic acid and the like. A physical stimulus such as heat or pressure during the detection of a nucleic acid can cause the detecting reagent to be exposed to a nucleic acid to bring the detecting reagent into contact with the nucleic acid, resulting in a color change.

Here, the coating material is not particularly limited as long as it can temporarily shield the detecting reagent. Examples thereof include polymer resins such as polyvinyl alcohol and polyethylene glycol, fat and oil such as paraffins, sugars such as agarose, gellan gum, carrageenan, xanthane gum, cluster dextrin, and hyaluronic acid, and proteins such as gelatin and collagen.

The present invention also relates to a device or kit for detecting a nucleic acid, including a carrier carrying a detecting reagent and a lid and/or a reaction container which are to be provided with the carrier.

The lid and/or reaction container included in the detection device are not particularly limited as long as they can form a closed system. The device may, for example, be one obtained by integrally molding a lid for sealing the opening of a reaction container with a joint between the upper part of the reaction container and the lid (a lid form-integrated reaction container type detection device and a reaction container form detection device), or a lid of a reaction container (a lid form detection device).

The reaction container is not particularly limited in form as long as it can carry a liquid and seal it with a lid or the like. Examples of the form of the reaction container include a tube form, plate form, film form, and chip form, which are used in PCR, gene manipulation, and the like. The reaction container may be a commercially available one. The bore, size, thickness and other properties of the reaction container may be appropriately set according to the mechanism of the nucleic acid amplification reaction or the like or the size of apparatus to be used. The reaction containers may be used alone, or a plurality of reaction containers, for example, four, eight, or twelve reaction containers may be combined.

The lid is not particularly limited as long as it can seal the opening of the corresponding reaction container. Examples thereof include those which are inserted inside the container to act as a seal, seals, films, and screw caps. The lid may be a commercially available one.

The lid preferably includes: a cylindrical sealing part formed such that it fits the opening of the reaction container to provide a suitable seal against the inner wall surface of the tube extending downwardly from the rim of the opening; and a peripheral part formed all around the edge of the cylindrical sealing part such that it comes into close contact with the edge of the reaction container to form a suitable seal against the edge so as to provide a closed system. The cylindrical sealing part is preferably designed to have higher sealing performance when attached to the opening of the reaction tube.

The materials of the lid and the reaction container are not particularly limited, and are preferably plastics. Plastics can be molded into a tube container by a conventionally known method such as injection molding, and allow bulk production at a low cost. Examples of the plastics include polyethylene resins, polypropylene resins, other polyolefin resins, polyester resins, fluorine resins, and silicon resins.

The detecting reagent carrier is fixed on the inside(s) of the lid and/or reaction container, and carries a detecting reagent for detecting a nucleic acid. The carrier may be fixed on either or both of the lid and the reaction container. In the reaction container and the lid, the position to fix the carrier is not particularly limited as long as it is able to contact a nucleic acid solution. It is desirable to appropriately adjust the position according to the structures of the reaction container and the lid to be used.

The lid and/or reaction container preferably carry a nucleic acid amplification reagent. The nucleic acid amplification reagent may be a reagent usable in nucleic acid amplification such as LAMP or PCR method. The detecting reagent and the nucleic acid amplification reagent may be held in different positions as follows. For example, the lid carries a detecting reagent, while the reaction container carries a PCR reagent (e.g. polymerase).

The carrier may have any shape as long as it allows a detecting reagent to be brought into contact with a nucleic acid in a closed system during the detection. For example, the shape of the lid or reaction container may be changed to provide a structure for carrying the reagent. In this case, for example, the carrier may be formed such that it projects out from the inner wall of the reaction container or lid toward the interior of the tube container (projecting type). Alternatively, a recess extending from the inner wall toward the inside of the inner wall may be formed (recessed type). Those which have a flat surface without changing the shape may also be used. Moreover, the reaction container or lid may be provided with a structure for temporarily shielding a detecting reagent (temporary shielding type). In this case, the shield may be lifted by a physical stimulus such as heat to allow the detecting reagent to contact a nucleic acid. Other than the lid and reaction container, materials such as a filter, a filter paper, a capsule, and a ring can be used to carry a detecting reagent.

The projecting type is one which includes a carrier projecting out from the inner wall surface of the lid or reaction container toward the interior thereof. The number of projections is not particularly limited, and is preferably 1 or 2. The shape of the projecting type when viewed from above is not particularly limited, and is preferably circular. When viewed in the cross-section of the lid or reaction container, the shape is, for example, a strip shape; a triangular shape in which the end projecting toward the interior of the container is pointed; a trapezoidal shape in which the end is flat; a dome shape in which the end is rounded; or a recessed shape in which the end is recessed toward the inner wall of the container. A structure may be formed such that the interior of the lid or reaction container is divided. It is desirable to appropriately adjust the size of the carrier according to the structures of the lid and the reaction container to be used.

The recessed type is one which includes a recess formed in the inner wall of the lid or reaction container. The number of recesses is not particularly limited, and is preferably 1 or 2. The shape of the recessed type when viewed from above is not particularly limited, and is preferably circular. When viewed in the cross-section of the lid or reaction container, the shape is, for example, a stripe shape; a triangular shape in which the end projecting toward the interior of the container is pointed; a trapezoidal shape in which the end is flat; a dome shape in which the end is rounded; or a recessed shape in which the end is recessed toward the inner wall of the container. The recessed type can be used in combination with the projecting type described above.

The shape, size, and number of the carrier are set in consideration of various factors including ease of manufacture of the lid and the reaction container, ease in bonding a dried reagent, and ease in charging or inserting a reagent into the recess or between the projections when the reagent is dried and solidified in the container.

The temporary shielding type has a structure for temporarily shielding a detecting agent from a nucleic acid in the lid or reaction container. The structure for shielding is not particularly limited as long as it can temporarily shield a detecting reagent. Examples of the structure include those which are used as coating materials, such as polymer resins such as polyvinyl alcohol and polyethylene glycol, fat and oil such as paraffins, sugars such as agarose, gellan gum, carrageenan, xanthane gum, cluster dextrin, and hyaluronic acid, proteins such as gelatin and collagen and the like. Examples thereof also include a structure which, before the detection of a nucleic acid, shields a detecting reagent from the nucleic acid and, during the detection, exposes the detecting reagent to the nucleic acid via a physical stimulus such as heat to allow the reagent to contact the nucleic acid. Here, the temporary shielding type may be a carrier combined with the structure of projecting type or recessed type. Or, it can be provided with the lid or reaction container which does not include such a structure.

In the following, some embodiments of the detection device of the present invention are described referring to figures.

Figure 1B:
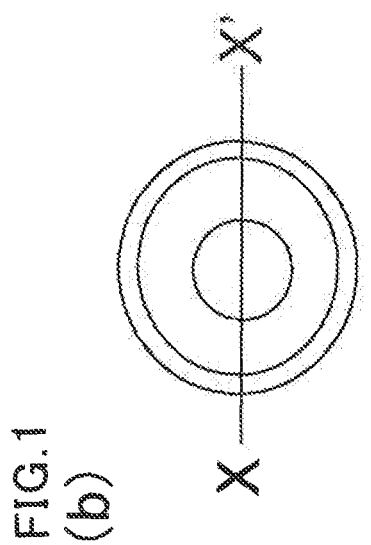
FIG. 1(b) is a schematic view illustrating the device shown in FIG. 1 (a) when viewed from the opening side.
Figure 1C:
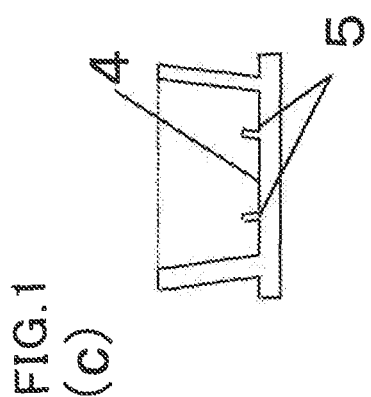
FIG. 1(c) is a schematic view illustrating the device shown in FIG. 1(a) cut along the line X-X' shown in FIG. 1(b) when viewed from the lateral side with the opening up.

FIG. 1 shows an appearance (a) of a detection device (lid form, projecting type I), a plane view (b) from the opening side of the device shown in (a), and a longitudinal sectional view (c) taken along the line X-X' shown in (b). The lid form, projecting type I device includes a bottom 1, an opening 2, a cylindrical body 3, a reagent carrier 4, and a wall 5 forming the carrier. The diameter of the body increases from the bottom toward the opening such that the body has higher sealing performance when inserted in a reaction container. The height of the body is preferably not greater than the length of the reaction container. The detecting reagent carrier may have any shape as long as it has a structure capable of carrying a detecting reagent. Examples of the shape include a strip shape; a triangular shape in which the end projecting toward the interior of the container is pointed; a trapezoidal shape in which the end is flat; a dome shape in which the end is rounded; and a recessed shape in which the end is recessed toward the inner wall of the container as described above. The wall and the diameter are not particularly limited as long as its height enables a detecting reagent to be held. The length is preferably not greater than the length of the body, and the diameter is preferably not greater than that of the opening.

Figure 2:
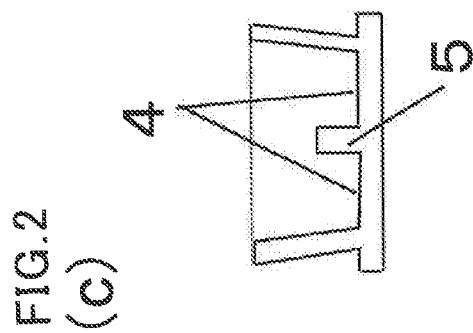
FIG. 2 (a) is a schematic view of a detection device (lid form, projecting type II).
Figure 2:
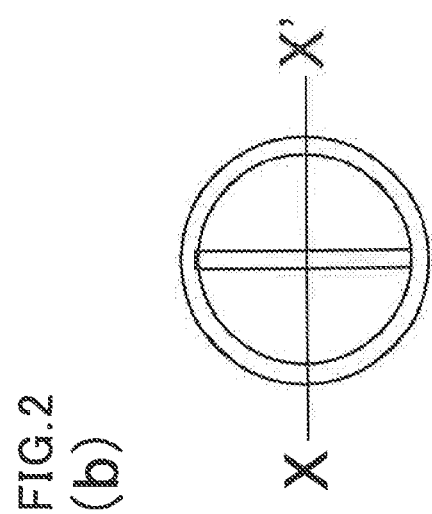
Figure 2:
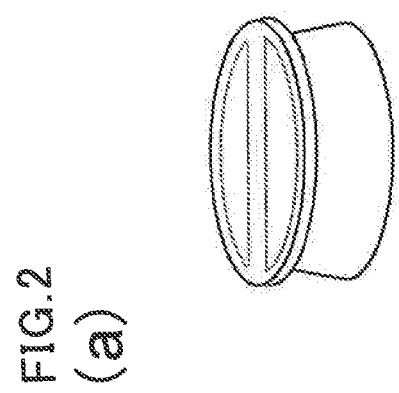

FIG. 2 shows an appearance (a) of a detection device (lid form, projecting type II), a plane view (b) from the opening side of the device shown in (a), and a longitudinal sectional view (c) taken along the line X-X' shown in (b). The lid form, projecting type II device includes, as in the case of the lid form, projecting type I device shown in FIG. 1, a bottom, an opening, a body, a reagent carrier, and a wall forming the carrier. However, the reagent carrier is different from that in the lid form, projecting type I, and the wall 5 is provided so as to divide the interior of the body into at least two sections. The height of the wall is not particularly limited as long as it enables a detecting reagent to be held. The height is preferably not greater than the length of the body.

Figure 3:
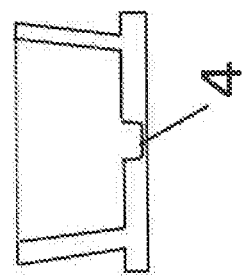
FIG. 3(a) is a schematic view of a detection device (lid form, recessed type).
FIG. 3(b) is a schematic view illustrating the device shown in FIG. 3 (a) when viewed from the opening side.
FIG. 3(c) is a schematic view illustrating the device shown in FIG. 3(a) cut along the line X-X' shown in FIG. 3(b) when viewed from the lateral side with the opening up.
Figure 3:
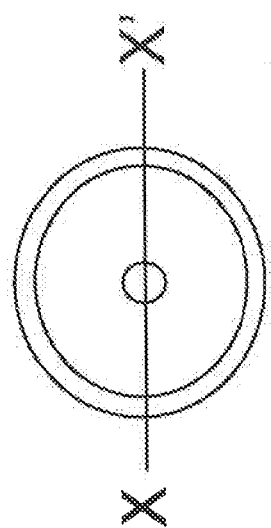
Figure 3:
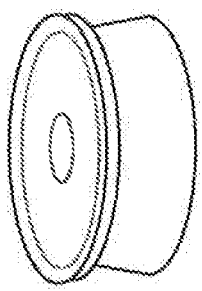

FIG. 3 shows an appearance (a) of a detection device (lid form, recessed type), a plane view (b) from the opening side of the device shown in (a), and a longitudinal sectional view (c) taken along the line X-X' shown in (b). The lid form, recessed type device includes, as in the case of the detection devices shown in FIGS. 1 and 2, a bottom, an opening, a body, a reagent carrier, and a wall forming the carrier. The carrier 4 forms a recess extending from the opening toward the bottom. The depth and the diameter of the recess are not particularly limited as long as they enable a detecting reagent to be held. The depth is preferably not greater than the thickness of the bottom, and the diameter is preferably not greater than the length of the opening.

Also, a lid form detection device including a reagent carrier combining projecting type and recessed type carriers can be prepared.

Figure 4:
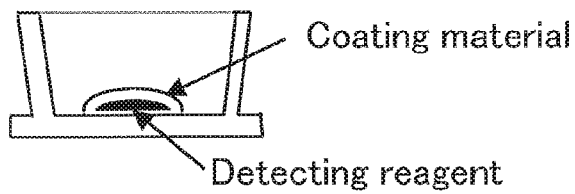
FIG. 4 is a schematic view of a detection device (lid form, temporary shielding type) when viewed from the lateral side with the opening up.

FIG. 4 shows a cross-sectional view of a detection device (lid form, temporary shielding type). In this case, a detecting reagent is coated with a coating material. The reagent carrier of the temporary shielding type may be combined with a projecting type or recessed type carrier.

Figure 7:
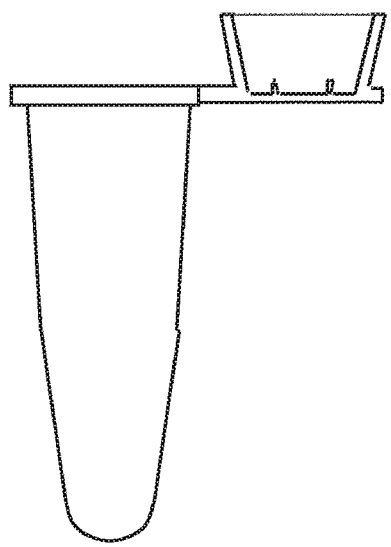
FIG. 7 is a schematic view of a detection device (lid form-integrated reaction container).

FIG. 7 shows an appearance of a detection device (lid form, projecting type I). Instead of the devices shown in FIGS. 1 to 3 that include a lid separate from a reaction container, a device in which a lid including a reagent carrier is integrated with a reaction container, as shown in FIG. 7, can be used. A plurality of the integrated type devices can be joined together. The joined devices facilitate simultaneous parallel processing of a plurality of samples.

FIG. 9 shows an appearance (a) of a detection device (reaction container form I), a longitudinal sectional view (b) taken along the line Y-Y' shown in (a), a longitudinal sectional view (c) of a reaction container form device including a recessed type reagent carrier, and a longitudinal sectional view (d) of a reaction container form device including a projecting type reagent carrier. The recessed type carrier (c) forms a recess extending in the direction of the bottom of the reaction container. The depth and the diameter of the recess are not particularly limited as long as their lengths enable a detecting reagent to be held. The depth is preferably not greater than the thickness of the reaction container, and the diameter is preferably not greater than that of the bottom of the reaction container. In the projecting type (d), a wall is formed so as to extend in the direction of the opening side of the reaction container. The height of the wall is not particularly limited as long as it enables a detecting reagent to be held. The height is preferably not greater than the length of the reaction container.

Figure 10:
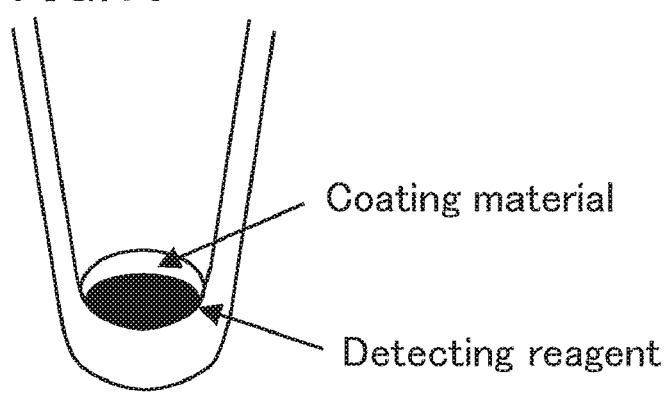
FIG. 10 is a schematic view of a reagent carrier of a detection device (reaction container form, temporary shielding type).

FIG. 10 shows a cross-sectional view of a detection device (reaction container form, temporary shielding type). In this case, a detecting reagent is held in a reagent carrier on a flat inner surface of a reaction container, and coated with a coating material described above. The reagent carrier of the temporary shielding type may be combined with a projecting type or recessed type carrier.

Figure 5:
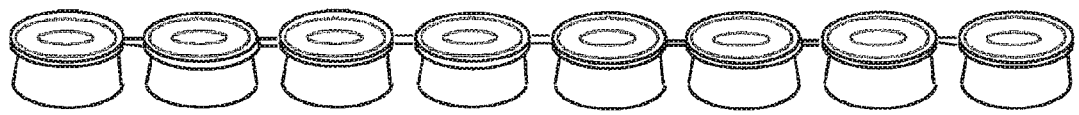
FIG. 5 is a schematic view of a device prepared by joining a plurality of the detection devices (lid form, projecting type I) shown in FIG. 1.

The detection devices may be used alone, or two or more of the detection devices may be joined together via a joint. The joined devices facilitate the detection of amplification products when a plurality of nucleic acid amplification reactions are carried out in parallel. The number of devices to be joined can be freely selected according to the situation of use. For example, FIG. 5 shows an appearance of lid form detection devices obtained by joining eight of the lid of the detection device shown in FIG. 1. The joint is formed to join a plurality of lids together, a plurality of connections together, a plurality of reaction containers together, or a combination thereof together, and is preferably formed to join lids together or reaction containers together. The joint in this case may be formed to join the edges of the openings of the reaction containers. Or alternatively, it may be formed to join the cylindrical bodies of the reaction containers.

The detecting reagent, the dye, and a modulator are fixed to the reagent carrier by the following method. The modulator means a component contained in the detecting reagent other than dyes, and examples thereof include nucleophilic agents, as well as stabilizers and coating agents. Examples of the nucleophilic agents include oxidizing agents, reducing agents, acids, bases, and pH buffers, which are used for enhancing the color contrast, as well as substances capable of converting a colored dye to a leuco dye.

At first, a solution prepared by dissolving a modulator in a solvent is charged into a reagent carrier and dried to be fixed. The method for drying is not particularly limited, and may be air drying, heating, drying under reduced pressure or the like. A combination of these methods may also be performed. The solvent may be any solvent capable of dissolving a modulator, and examples thereof include water, ethanol, methanol, and isopropanol. A base material such as a polymer may also be added to the solution in order to prevent the dried modulator from peeling or falling off. For example, polyvinyl alcohol may be added. The amount of the base material such as a polymer can be adjusted within a range allowing a color change of a nucleic acid to be observed when the base material is dried. The amount is preferably not more than 0.1 mg, and more preferably not more than 0.01 mg. Alternatively, the reagent may be held in the form of a viscous liquid sol, or in the form of a solid gel. In addition, a solubilizing agent or the like may be added in order to increase solubility of the dried modulator. Examples thereof include surfactants such as Triton X-100 and Tween 20, cyclodextrin, and β-glucan. In this case, the amount of the modulator can be adjusted within a range allowing a color change of a nucleic acid to be observed when the modulator is dried. The amount is preferably, for example, 1000 molar equivalents or less, and more preferably 100 molar equivalents or less, relative to the amount of the dye.

Here, if a solution containing a nucleic acid contains a modulator, only a dye may be fixed. The order of fixing the modulator and the dye is not limited. A mixture of a modulator solution and a dye solution may be used to fix the modulator and the dye at one time.

In preparing a detection device with a temporary shielding type reagent carrier, a coating is formed in the following method.

First, a coating material described above is melted and poured onto a dried detecting reagent and then cooled to be fixed. Or alternatively, the coating material is dissolved into a solvent and the resulting solution is poured onto a dried detecting reagent and then dried to be fixed. The coating material is not particularly limited as long as it can stably cover the detecting reagent but can release the reagent through a physical treatment such as heating. Examples thereof include solid paraffins, polyvinyl alcohol, polyethylene glycol, agarose, gellan gum, carrageenan, xanthane gum, and hyaluronic acid. Preferred are paraffins and polyvinyl alcohol.

Here, the reagent carrier may carry various reagents required for amplifying a nucleic acid, along with the detecting reagent. Examples of the various reagents include primers and DNA polymerases for amplifying a target nucleic acid according to the nucleic acid amplification method described above, buffers usable for the nucleic acid amplification reaction, and restriction enzymes. In this case, the detecting reagent and the reagent for amplification may be separately held in a lid and a reaction container. Each of the reagents may be shielded by a wall of the reagent carrier or a temporary shielding type carrier.

In the following, the method for detecting a nucleic acid using the detection device is described referring to drawings.

Figure 6:
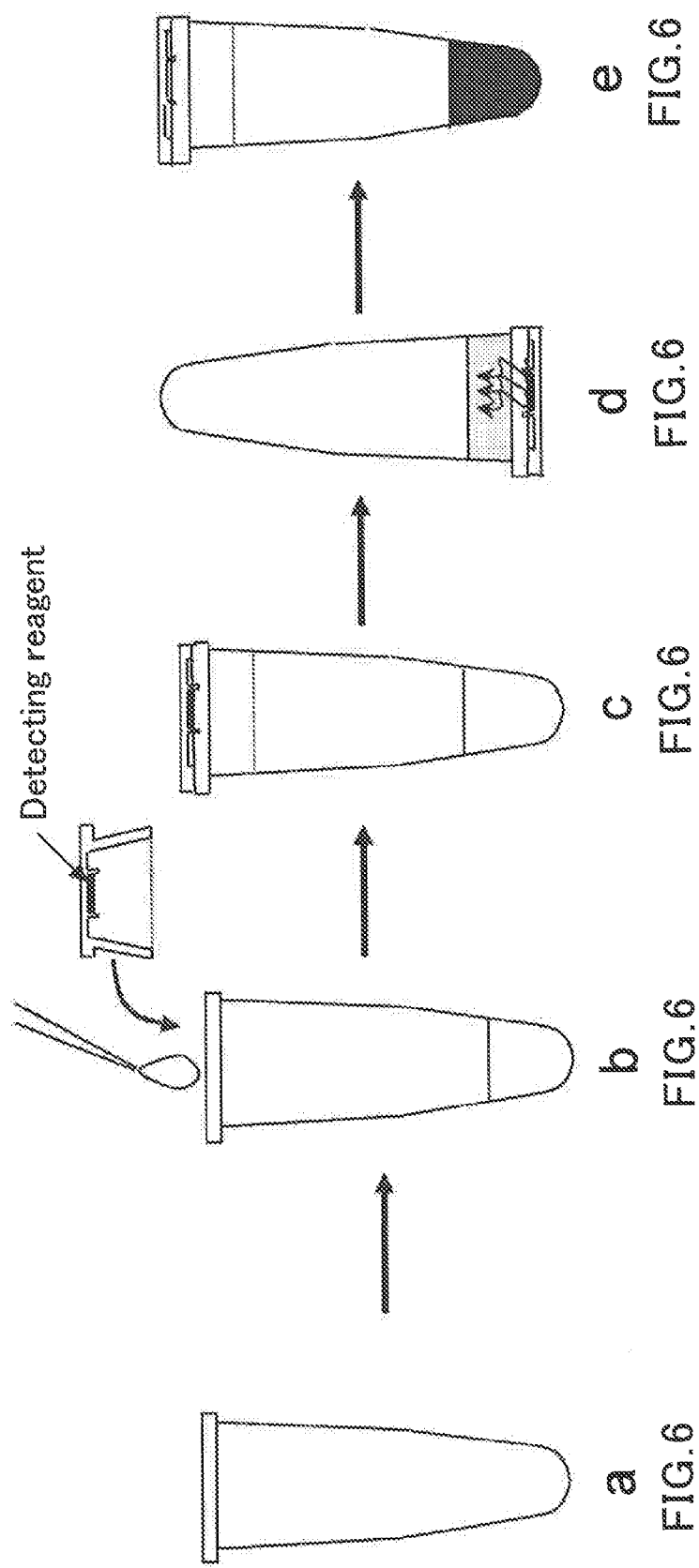
FIGS. 6a-6e illustrate a process of detecting a nucleic acid using each of the detection devices (lid form) shown in FIGS. 1 to 5.

FIG. 6 shows a process of detecting a nucleic acid using a lid form detection device (a). A nucleic acid solution or a nucleic acid amplification reaction mixture is charged into a reaction container, and the container is covered with a detection device carrying a detecting reagent as a lid (step (b)). A nucleic acid amplification reaction and other reactions are then performed as necessary (step (c)). Thereafter, the detection device is turned upside down or subjected to other operations to contact the detecting reagent with the solution containing a nucleic acid and dissolve the reagent in the nucleic acid solution so as to color the nucleic acid (steps (d) and (e)). During this step, stirring such as vortexing may be performed to efficiently dissolve the reagent. If a PCR reaction is performed using a palm-sized ultracompact PCR device, the device itself, after the amplification reaction, can be turned upside down so as to contact the reaction solution with the detecting agent to perform the detection.

Figure 8:
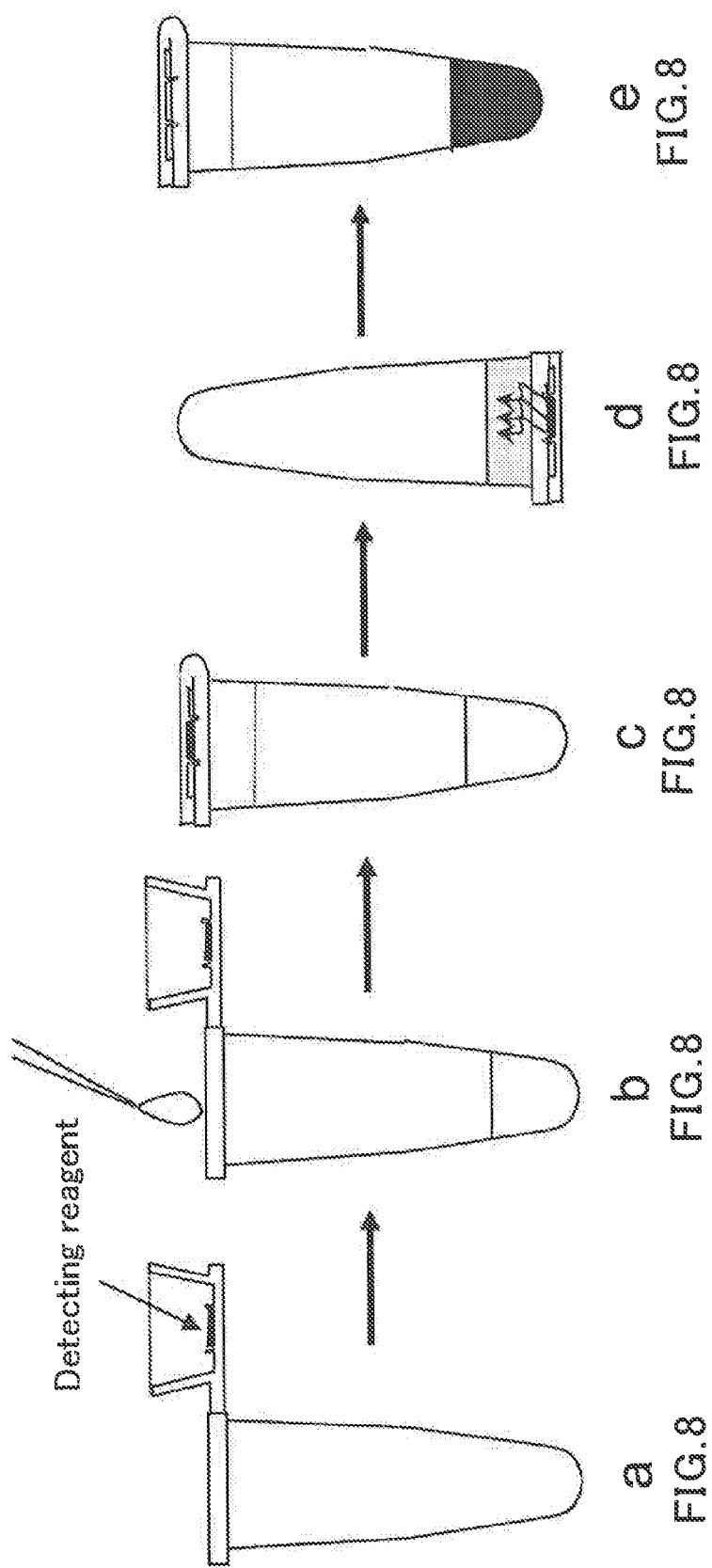
FIGS. 8a-8e illustrate a process of detecting a nucleic acid using the detection device (lid form-integrated reaction container) shown in FIG. 7.

FIG. 8 shows a process of detecting a nucleic acid using a lid form-integrated reaction container type detection device (a). A nucleic acid solution or a nucleic acid amplification reaction mixture is charged into a detection device carrying a detecting reagent, followed by closing a lid (step (b)). Thereafter, the device is subjected to the same operations as for the lid form detection device.

Figure 11:
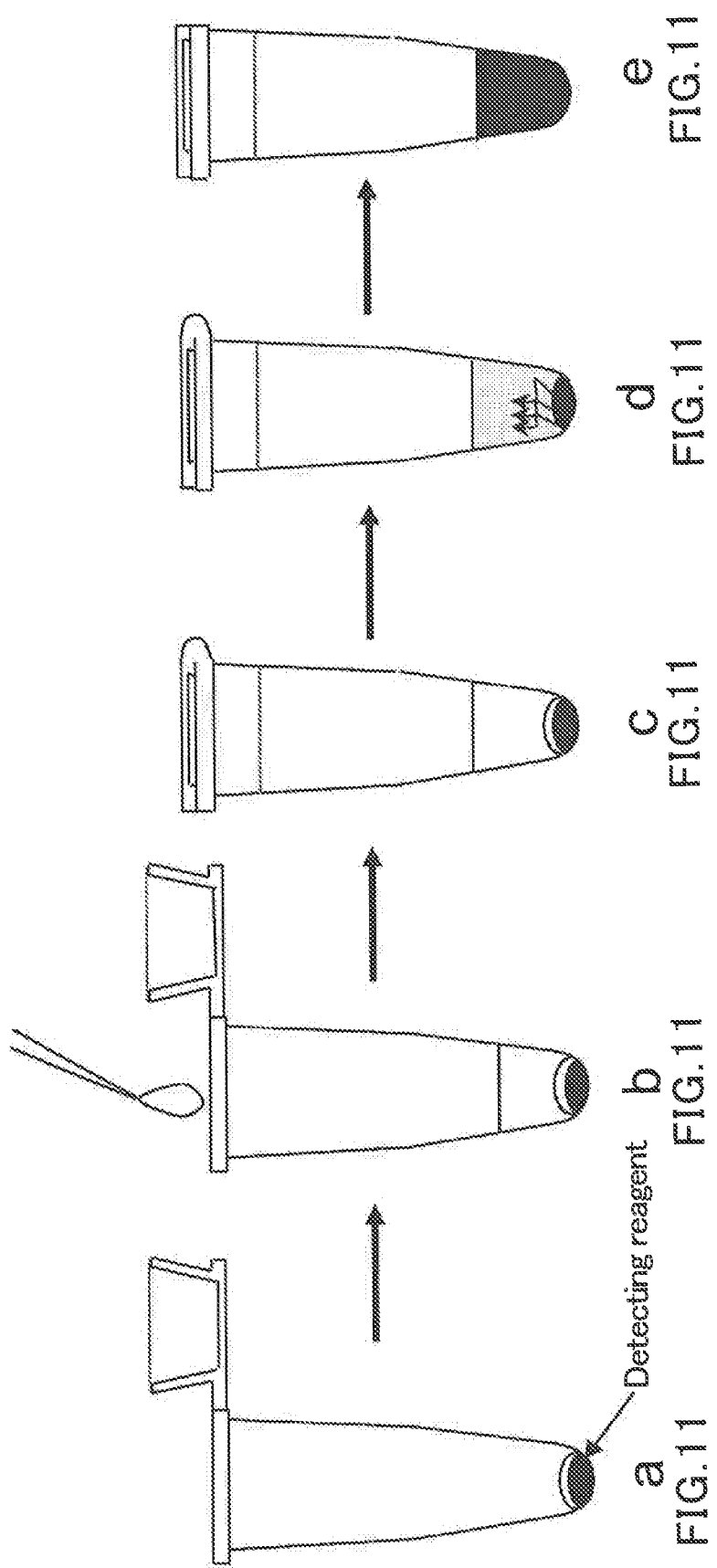
FIGS. 11a-11e illustrate a process of detecting a nucleic acid using the detection device (reaction container form, temporary shielding type) shown in FIG. 10.

FIG. 11 shows a process in which a reaction container form detection device (a) including a temporary shielding type reagent carrier is used. A nucleic acid solution or a nucleic acid amplification reaction mixture is charged into a reaction container carrying a detecting reagent (step (b)), followed by closing a lid. A nucleic acid amplification reaction and other reactions are performed as necessary (step (c)). Thereafter, the detecting reagent inside a coating material is dissolved into the nucleic acid solution through a treatment such as heating. The heating temperature is not particularly limited as long as it causes the coating material to physically change so that the detecting reagent can contact the nucleic acid solution. The heating temperature is preferably 40° C. or higher, and more preferably 60° C. or higher.

Figure 12:
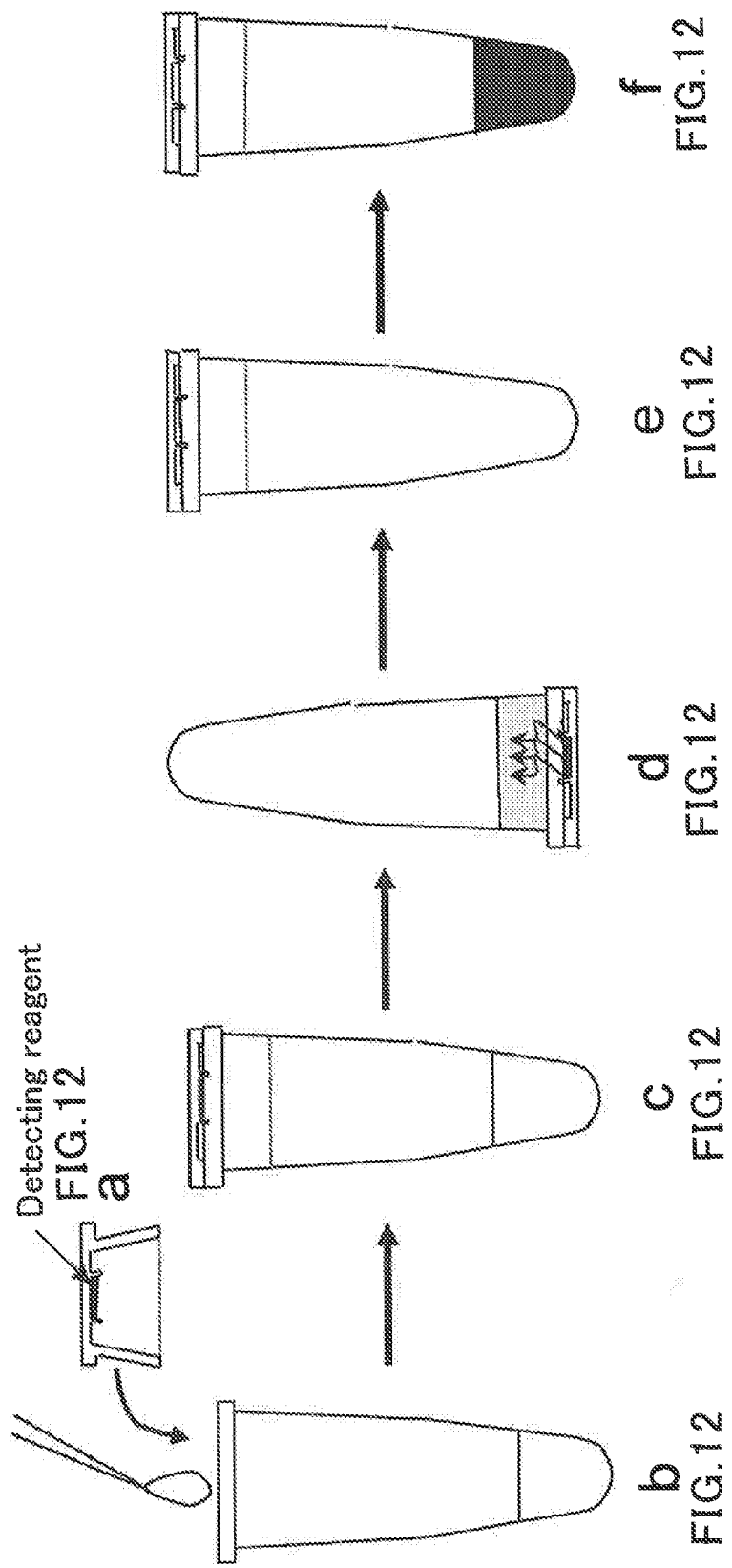
FIGS. 12a-12f illustrate a process of detecting a nucleic acid using a detection device (lid form).

FIG. 12 shows a process of detecting a nucleic acid using a lid form detection device (a). An amplification reaction mixture is prepared in a container (step (b)), and the container is covered with a lid carrying a detecting reagent (step (c)). Thereafter, the detection device is turned upside down or subjected to other operations to contact the detecting reagent with the reaction mixture and dissolve the reagent (step (d)). During this step, stirring such as vortexing may be performed to efficiently dissolve the reagent. Thereafter, the solution is spun down using a centrifuge or the like to collect the solution attached to the lid into the container, and an amplification reaction is then performed.

Figure 13:
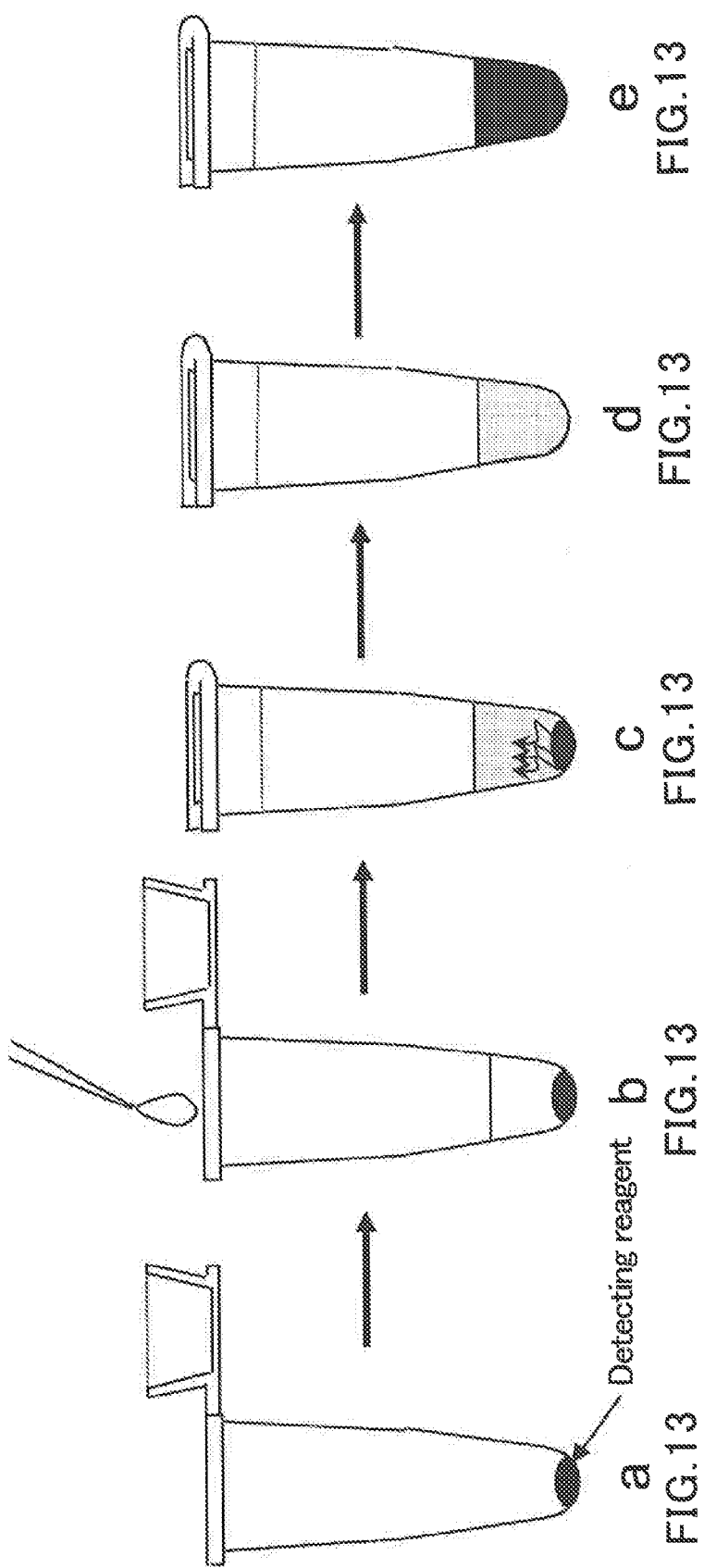
FIGS. 13a-13e illustrate a process of detecting a nucleic acid using a detection device (reaction container form).

FIG. 13 shows a process in which a reaction container form detection device (a) is used. An amplification reaction solution is prepared in a container, and a detecting reagent held in the reaction container is dissolved in the solution (step (b)). Or alternatively, a reaction solution prepared in a separate container may be charged into the detection device. Thereafter, an amplification reaction is performed by thermal cycling or the like.

In the following, the step of detection under visible light after the step (e) in FIGS. 6, 8, 11, 12, and 13 is described.

In observing a substance formed through the reaction in the step (e) under visible light to identify the presence of a nucleic acid under visible light, the substance is observed under visible light such as common lighting in experimental laboratories, without irradiation with light other than visible light, such as ultraviolet light. The use of visible light allows simple observation as it requires no special device, unlike in the case of ultraviolet light irradiation.

Here, with the detection device, the steps (c) to (e) shown in FIGS. 6, 8, 11, 12, and 13 and the detection step can be performed fully automatically. The phrase "fully automatically" means that a process is included in which the reaction and the detection step are automatically performed using the detection device of the present invention.

For example, in the lid form detection device shown in FIG. 6 and the lid form-integrated reaction container type detection device shown in FIG. 8, a nucleic acid solution or a nucleic acid amplification reaction mixture is charged into a reaction container carrying a detecting reagent (step (b)), followed by closing a lid. Subsequent steps can be automatically performed by use of an apparatus which can control the temperature and optionally can vibrate, shake, and invert the reaction container. A nucleic acid amplification reaction and other reactions are performed as necessary (step (c)). Thereafter, the detection device is shaken or inverted or subjected to other operations to contact the detecting reagent in the lid with the solution containing a nucleic acid to cause coloring. Further, if necessary, irradiation with visible light, which is incorporated in the apparatus, may be performed to determine the presence or absence of coloring and the degree of coloring, and if necessary, analyze the data.

In the process of FIG. 11 in which a reaction container form detection device including a temporary shielding type reagent carrier is used, a nucleic acid solution or a nucleic acid amplification reaction mixture is charged into a reaction container carrying a detecting reagent (step (b)), followed by closing a lid. Subsequent steps are automatically performed by use of the apparatus described above. A nucleic acid amplification reaction and other reactions are performed as necessary (step (c)). Thereafter, the detecting reagent inside a coating material can be dissolved into the nucleic acid solution through a treatment such as heating, to cause coloring. Further, if necessary, irradiation with visible light may be performed to determine the presence or absence of coloring and the degree of coloring.

In the present invention, a colored sample liquid obtained through the detection of a nucleic acid may be directly used in other molecular biological operations. Examples of the molecular biological operations include enzyme reactions such as a restriction enzyme reaction, sequencing reaction and PCR, and confirmation by electrophoresis.

The present invention encompasses a kit including the device for detection under visible light, in combination with reagents, implements and the like. The kit refers to a form including various reagents, implements and the like, in addition to the detection device. Examples of the various reagents include primers and DNA polymerases for amplifying a target nucleic acid according to the nucleic acid amplification method described above, buffers usable for the nucleic acid amplification reaction, restriction enzymes for processing an amplified nucleic acid, and reagents for sequencing. With the use of an antigen, antibody, dye, enzyme, substrate, or the like, the kit of the present invention can also be used in measurement of an immune reaction or biochemical reaction and in trace detection by an immunofluorescent method.

The present invention encompasses an apparatus including the device for detection under visible light or the kit. The apparatus automatically processes a sample and analyzes the base sequence or the like, and includes the detection device of the present invention. For example, the device for detection under visible light of the present invention may be incorporated in an apparatus for purifying a nucleic acid or an apparatus for amplifying a nucleic acid to identify the presence or absence of a nucleic acid. The device of the present invention may also be incorporated in an automatic DNA analysis apparatus to selectively analyze a sample amplified or labeled by PCR. As above, increased assurance of operation can be expected.

EXAMPLES

In the following, the present invention is more specifically described referring to, but not limited to, examples.

Example 1

(i) Preparation of a Lid Form Detection Device Including a Lid Form, Recessed Type Reagent Carrier Using a rotary file, two recesses having a diameter of 0.5 mm were formed on the inner side of a lid of a 0.2-ml PCR tube to provide reagent carriers. An amount of 1 µl of a dye solution (a 0.2% solution of gentian violet B in ethanol) was charged into one of the reagent carriers, and 1 µl of a reducing agent solution (a 3.2% sodium sulfite/1% polyvinyl alcohol aqueous solution) was charged into the other carrier. Thereafter, the solutions were dried under reduced pressure. In this manner, a reaction container carrying a nucleic acid detecting reagent was obtained.

(ii) Detection of PCR Amplified Product

Using pUC19 (produced by Takara Bio Inc.) as a template, the primer F: 5'-GGAAACAGCTATGACCATGA-3' and the primer R: 5'-CTATGCGGCATCAGAGCAG-3' were designed to amplify about 330 base pairs through PCR amplification.

An amount of 15 pmol of the primer F, 15 pmol of the primer R, and 10 ng of pUC19 were placed in the reaction container prepared in the step (i), and 50 µl of a PCR reaction mixture was then prepared in accordance with the description of ExTaq PCR kit (produced by Takara Bio Inc.). Subsequently, the tube was set in a thermal cycler (GeneAmp PCR System (produced by Applied Biosystems)), and heat-treated at 95° C. for 5 minutes and then exposed to 35 cycles of 95° C. for 30 seconds, 55° C. for 30 seconds, and 72° C. for 30 seconds. In this manner, the desired amplification of about 330 bp was performed to provide a positive control. Separately, the same reaction was performed without adding ExTaq DNA polymerase to provide a negative control.

After the PCR reaction, the container was inverted to mix the contents so as to dissolve the detecting reagent in the lid into the reaction solution. The color tone of the reaction solution was then visually observed. The results show that the negative control was colorless, whereas the positive control turned blue. Thus, the presence or absence of nucleic acid amplification was identifiable without opening and/or closing the lid of the reaction container.

(iii) Detection of LAMP Amplified Product

Using a "Loopamp (R) Salmonella Detection Reagent Kit" (produced by Eiken Chemical Co., Ltd.), a LAMP nucleic acid amplification reaction mixture was prepared in the reaction container prepared in the step (i). An amount of 10 µl of Control DNA Sal and 40 µl of Master Mix (a mixture separately prepared by mixing Reaction Mix. Sal and Bst DNA Polymerase at a volume ratio of 20:1) were mixed and reacted at 65° C. for 1 hour and then at 85° C. for 20 minutes to prepare a reaction mixture (positive control) with an amplified nucleic acid. Separately, 10 µl of distilled water and 40 µl of Reaction Mix. Sal were mixed and reacted at 65° C. for 1 hour and then at 85° C. for 20 minutes to prepare a reaction mixture (negative control) without an amplified nucleic acid.

After the reaction, the container was inverted to mix the contents so as to dissolve the detecting reagent in the lid into the reaction solution. The color tone of the reaction solution was then visually observed. The results shows that the negative control was colorless, whereas the positive control turned blue. This demonstrates that the presence or absence of nucleic acid amplification was identifiable without opening and/or closing the lid of the reaction container.

Example 2

(i) Preparation of a Reaction Container Form Detection Device Including a Recessed Type Reagent Carrier Using a rotary file, one recess having a diameter of 0.5 mm was formed on the inner side of a lid of a 0.2-ml PCR tube to provide a reagent carrier. An amount of 1 µl of a reducing agent solution (a 3.2% sodium sulfite/1% polyvinyl alcohol aqueous solution) was charged into the reagent carrier, and then dried under reduced pressure. Further, 1 µl of a dye solution (a 0.2% solution of gentian violet B in ethanol) was charged into the reagent carrier and then dried under reduced pressure. In this manner, a reaction container carrying a nucleic acid detecting reagent was obtained.

(ii) Detection of PCR and LAMP Amplified Products

A PCR amplified product and LAMP amplified product were prepared in the same manner as in the steps (ii) and (iii) of Example 1, except that reaction container prepared in the above step (i) was used. After the reaction, the container was inverted to mix the contents so as to dissolve the reagent in the lid into the reaction solution. The color tone of the reaction solution was then visually observed. The results show that the reaction solution became colored blue only when a nucleic acid amplification product obtained by PCR or LAMP method existed. Thus, the presence or absence of amplification was easily visually identifiable.

Example 3

(i) Preparation of a Reaction Container Form Detection Device Including a Recessed Type Reagent Carrier Using a rotary file, one recess having a diameter of 0.5 mm was formed on the inner side of a lid of a 0.2-ml PCR tube to provide a reagent carrier. An amount of 2 µl of a nucleic acid detecting reagent (0.1% gentian violet B/0.8% sodium sulfite/0.75% beta-cyclodextrin/35% isopropanol) was charged into the reagent carrier, and then dried under reduced pressure. In this manner, a reaction container carrying a nucleic acid detecting reagent was obtained.

(ii) Detection of PCR and LAMP Amplified Products

A PCR amplified product and LAMP amplified product were prepared in the same manner as in the steps (ii) and (iii) of Example 1, except that reaction container prepared in the above step (i) was used. After the reaction, the container was inverted to mix the contents so as to dissolve the reagent in the lid into the reaction solution. The color tone of the reaction solution was then visually observed. The results show that the reaction solution became colored blue only when a nucleic acid amplification product obtained by PCR or LAMP method existed. Thus, the presence or absence of amplification was easily visually identifiable.

Example 4

(i) Preparation of a Lid Form Detection Device Including a Temporary Shielding Type Reagent Carrier Using a rotary file, two recesses having a diameter of 0.5 mm were formed on the inner side of a lid of a 0.2-ml PCR tube to provide reagent carriers. An amount of 1 µl of a dye solution (a 0.2% solution of gentian violet B in ethanol) was charged into one of the recesses, and 1 µl of a reducing agent solution (a 3.2% sodium sulfite/1% polyvinyl alcohol aqueous solution) was charged into the other recess. The solutions were then dried under reduced pressure. Subsequently, a molten paraffin wax (melting point: 70° C. to 80° C.) was added dropwise onto the dried products and cooled to be solidified. In this manner, a reaction container with a lid carrying a paraffin-coated detecting reagent was obtained.

(ii) Detection of LAMP Amplified Product

Using the reaction container prepared in the step (i), LAMP reaction mixtures (positive control, negative control) were prepared in the same manner as in the step (iii) of Example 1. Then, each of the samples was reacted at 65° C. for 1 hour and then at 85° C. for 20 minutes. After the reaction, the lid was heated at 98° C. for 1 minute to melt the paraffin. Thereafter, the reaction container was inverted to mix the contents so as to dissolve the detecting reagent in the lid into the reaction solution. The color tone of the reaction solution was then visually observed. The results show that the negative control was colorless, whereas the positive control turned blue. This demonstrates that the presence or absence of nucleic acid amplification was identifiable without opening and/or closing the lid of the reaction container.

Example 5

(i) Preparation of a Reaction Container Form Detection Device Including a Temporary Shielding Type Reagent Carrier An amount of 1 µl of a reducing agent solution (a 3.2% sodium sulfite/1% polyvinyl alcohol aqueous solution) was charged to the bottom of the body of a 0.2-ml PCR tube, and then dried under reduced pressure. Further, 1 µl of a dye solution (a 0.2% solution of gentian violet B in ethanol) was charged into a reagent carrier thereof and then dried under reduced pressure. Thereafter, a molten paraffin wax (melting point: 70° C. to 80° C.) was added dropwise onto the dried products and cooled to be solidified. In this manner, a reaction container with a paraffin coating was obtained.

(ii) Detection of LAMP Amplified Product

Using the reaction container prepared in the step (i), LAMP reaction mixtures (positive control, negative control) were prepared in the same manner as in the step (iii) of Example 1. Then, each of the samples was reacted at 65° C. for 1 hour and then at 85° C. for 20 minutes. Here, the treatments at 65° C. and 85° C. were automatically performed in the same apparatus by programming the apparatus. The observation of the colors of the reaction solutions after the reaction demonstrated that the negative control was colorless, whereas the positive control turned blue. Thus, the presence or absence of nucleic acid amplification by LAMP method was easily visually identifiable without opening and/or closing the lid.

Example 6

(i) Preparation of a Plate Seal Carrying a Nucleic Acid Detecting Reagent

A reducing agent solution (a 3.2% sodium sulfite/1% polyvinyl alcohol aqueous solution) was charged to a plate seal for a 96-well PCR plate (produced by Thermo Fisher Scientific K.K.) such that 1 µl of the solution was placed in a position corresponding to the center of each well. The solution was dried under reduced pressure. Further, 1 µl of a dye solution (a 0.2% solution of gentian violet B in ethanol) was charged to each position and then dried under reduced pressure.

(ii) Detection of PCR Amplified Product

PCR reaction mixtures were prepared in the same manner as in the step (ii) of Example 1, except that a 96-well PCR plate and the plate seal prepared in the above step (i) were used.

After the PCR reaction, the plate was inverted to mix the contents so as to dissolve the detecting reagent in the lid into the reaction solution. The color tone of the reaction solution was then visually observed. The results show that the negative control was colorless, whereas the positive control turned blue. Thus, the presence or absence of nucleic acid amplification was identifiable without opening and/or closing the lid of the reaction container.

Example 7

(i) Preparation of a Reaction Container Form Detection Device Including a Temporary Shielding Type Reagent Carrier (PCR Reagent)

Reagents for PCR (except pUC19 as a template) used in the step (i) of Example 1 were charged to the bottom of a reaction container, a 0.2-ml PCR tube, and then dried under reduced pressure. Subsequently, a molten paraffin wax (melting point: 70° C. to 80° C.) was added dropwise onto the dried reagents and cooled to be solidified. In this manner, a reaction container carrying dried PCR reagents covered with a paraffin coating was obtained. An amount of 1 µl of a reducing agent solution (a 3.2% sodium sulfite/1% polyvinyl alcohol aqueous solution) was charged into a lid of the reaction container, and then dried under reduced pressure. Further, 1 µl of a dye solution (a 0.2% solution of gentian violet B in ethanol) was added onto the dried product and then dried under reduced pressure. Thereafter, a molten paraffin wax (melting point: 70° C. to 80° C.) was added dropwise thereto and cooled to be solidified to prepare a reaction container with a lid carrying a paraffin-coated detecting reagent. In this manner, a detection device which included a reaction container carrying paraffin-coated PCR reagents and a lid carrying a paraffin-coated detecting reagent was obtained.

(ii) Detection of PCR Amplified Product

An amount of 50 µl of an aqueous solution containing pUC19 was charged into the reaction container prepared in the step (i). An amplification reaction was then performed in the same manner as in the step (ii) of Example 1. After the PCR reaction, the container was inverted to mix the contents so as to dissolve the detecting reagent in the lid into the reaction solution. The color tone of the reaction solution was then visually observed. The results show that the negative control was colorless, whereas the positive control turned blue. Thus, the presence or absence of nucleic acid amplification was identifiable without opening and/or closing the lid of the reaction container.

Example 8

(i) Preparation of a Lid Form Detection Device Using a Commercially Available Tube An amount of 1 µl of a reducing agent solution (a 3.2% sodium sulfite/1% polyvinyl alcohol aqueous solution) was charged to the bottom of a rounded lid of a 0.2-ml PCR tube Dome-cap (produced by Watson). The solution was then dried under reduced pressure. Further, 1 µl of a dye solution (a 0.2% solution of gentian violet B in ethanol) was charged into a reagent carrier thereof and then dried under reduced pressure. Subsequently, a molten paraffin wax (melting point: 70° C. to 80° C.) was added dropwise and cooled to be solidified. In this manner, a reaction container with a paraffin coating was obtained.

(ii) Detection of LAMP Amplified Product

Using the Reaction Container Prepared in the Step (i), LAMP reaction mixtures (positive control, negative control) were prepared in the same manner as in the step (iii) of Example 1. Then, each of the samples was reacted at 65° C. for 1 hour and then at 85° C. for 20 minutes. Here, the treatments at 65° C. and 85° C. were automatically performed in the same apparatus by programming the apparatus. The observation of the colors of the reaction solutions after the reaction demonstrated that the negative control was colorless, whereas the positive control turned blue. Thus, the presence or absence of nucleic acid amplification was easily visually identifiable without opening and/or closing the lid.

Example 9

(i) Preparation of a Reaction Container Form Detection Device Including a Temporary Shielding Type Reagent Carrier An amount of 5 µl of a nucleic acid detecting reagent (0.068% gentian violet B/0.4% sodium sulfite/0.24% beta-cyclodextrin/1.2% polyvinyl alcohol (polymerization degree: 500)/1.2% cluster dextrin/20% ethanol) was charged into each of lids of 8-PCR tube Strip. The solution was then dried under reduced pressure.

(ii) Detection of LAMP Amplified Product

Using the reaction containers prepared in the step (i), LAMP reaction mixtures (positive control, negative control) were prepared in the same manner as in the step (iii) of Example 1. Then, each of the samples was reacted at 65° C. for 1 hour and then at 85° C. for 20 minutes. Here, the treatments at 65° C. and 85° C. were automatically performed in the same apparatus by programming the apparatus. The observation of the colors of the reaction solutions after the reaction demonstrated that the negative control was colorless, whereas the positive control turned blue. Thus, the presence or absence of nucleic acid amplification was easily visually identifiable without opening and/or closing the lid.

Example 10

(i) Preparation of a Reaction Container Form Detection Device Including a Temporary Shielding Type Reagent Carrier An amount of 1 µl of a nucleic acid detecting reagent (0.1% gentian violet B/2% sodium sulfite/1.2% beta-cyclodextrin/40% ethanol) was charged into each of lids of 8-PCR tube Strip. The solution was then dried under reduced pressure. Subsequently, a solution of 2% polyvinyl alcohol (polymerization degree: 1000) in 40% ethanol was added dropwise onto the dried product and dried under reduced pressure. In this manner, reaction containers with lids carrying a detecting reagent coated with polyvinyl alcohol were obtained.

Master Mix for LAMP (a mixture prepared by mixing Reaction Mix. Sal and Bst DNA Polymerase at a volume ratio of 20:1) used in the step (iii) of Example 1 was charged to each bottom of the reaction containers of the 8-PCR tube Strip. The Master Mix was then dried under reduced pressure. In this manner, eight devices joined together were obtained, each of which included a reaction container carrying a LAMP reagent and a lid carrying a detecting reagent coated with polyvinyl alcohol.

(ii) Detection of LAMP Amplified Product

Using the reaction containers prepared in the step (i), LAMP reaction mixtures (positive control, negative control) were prepared in the same manner as in the step (iii) of Example 1. Then, each of the samples was reacted at 65° C. for 1 hour and then at 85° C. for 20 minutes. Here, the treatments at 65° C. and 85° C. were automatically performed in the same apparatus by programming the apparatus. The observation of the colors of the reaction solutions after the reaction demonstrated that the negative control was colorless, whereas the positive control turned blue. Thus, the presence or absence of nucleic acid amplification was easily visually identifiable without opening and/or closing the lid.

Example 11

Detection of LAMP Method

Using a "Loopamp DNA amplification kit" (produced by Eiken Chemical Co., Ltd.), LAMP nucleic acid amplification reaction mixtures were prepared as follows. Here, the attached protocol was partially modified. An amount of 12.5 µl of Reaction Mix, 2.5 µl of Primer Mix, 1 µl of Bst DNA Polymerase, 6 µl of distilled water, and 1 µl of a nucleic acid detecting reagent (0.1% gentian violet B, 2.1% sodium sulfite, 1.5% β-cyclodextrin) were charged into each of 0.2-ml microfuge tubes. Further, 2 µl of Positive Control DNA (positive control) or 2 µl of distilled water (negative control) was added to the tube to give a total of 25 µl. Each of the reaction mixtures was well mixed by vortexing, and spun down. The microfuge tubes were incubated at 63° C. for 60 minutes to perform an amplification reaction, followed by incubation at 80° C. for 5 minutes. Then, the reaction was terminated.

The visual observation of the color tones of the reaction solutions after the amplification reaction demonstrated that the negative control was nearly colorless, whereas the positive control turned blue. This shows that the present detecting reagent did not considerably inhibit the LAMP reaction when it coexisted in the reaction mixture during the LAMP reaction, and that the presence or absence of nucleic acid amplification was identifiable by simply observing the solution after the reaction.

Example 12

Detection of LAMP Method in which Pyrophosphatase is Added

In order to perform a nucleic acid amplification reaction in which pyrophosphatase was used to suppress the formation of pyrophosphoric acid, a by-product of the amplification reaction, LAMP reaction mixtures were prepared using an "Isothermal Master Mix" (produced by OptiGene) instead of the Reaction Mix used in Example 11. The positive control and negative control were incubated at 63° C. for 30 minutes to perform an amplification reaction, followed by incubation at 80° C. for 5 minutes. Then, the reaction was terminated.

The visual observation of the color tones of the reaction mixtures after the amplification reaction demonstrated that the negative control was nearly colorless, whereas the positive control turned blue. In addition, since pyrophosphoric acid was degraded by pyrophosphatase, the reactivity was improved, and therefore shortening of the time required for coloring was enabled.

Example 13

Preparation of a Lid Form Detection Device and Detection of LAMP Reaction

Using a rotary file, a recess having a diameter of 0.5 mm was formed on the inner side of a lid of a 0.2-ml PCR tube to provide a reagent carrier. An amount of 1 µl of a detecting reagent (0.1% gentian violet B, 2.1% sodium sulfite, 1.5% β-cyclodextrin) was charged into the reagent carrier, and then dried under reduced pressure. In this manner, a reaction container carrying a nucleic acid detecting reagent was obtained.

Using the thus obtained reaction container, LAMP reaction mixtures were prepared in the same manner as in Example 11, except that the detecting reagent was added. The reaction container was inverted to mix the contents so as to contact the reaction mixture with the detecting reagent held in the reagent carrier, so that the reagent was completely dissolved. After spinning down, the reaction container was incubated at 63° C. for 60 minutes to perform an amplification reaction, followed by incubation at 80° C. for 5 minutes. Then, the reaction was terminated.

The visual observation of the color tones of the reaction solutions after the amplification reaction demonstrated that the negative control was nearly colorless, whereas the positive control turned blue.

Example 14

(i) Preparation of a Lid Form Detection Device

A LAMP reaction reagent (14 mM dNTPs, 4 µM FIP, 4 µM BIP, 0.5 µM F3, 0.5 µM B3, 40 U Bst DNA Polymerase) was prepared. An amount of 10 µl of the prepared reaction reagent was charged into each of the bodies of 0.2-ml PCR tubes. An amount of 1 µl of a detecting reagent (0.1% gentian violet B, 2.1% sodium sulfite, 1.5% β-cyclodextrin, 0.15% ascorbic acid) was charged to the inner side of each lid of the tubes. The thus-dispensed reaction reagent and detecting reagent were dried under reduced pressure. In this manner, reaction containers each carrying a LAMP reaction reagent and a detecting reagent were obtained.

(ii) Preparation of a Reaction Container Form Detection Device

A solution was prepared by mixing the reaction reagent and the detecting reagent used in the step (i), and then 10 µl of the solution was charged into each of the bodies of PCR tubes and dried under reduced pressure. In this manner, reaction containers each carrying a LAMP reaction reagent and a detecting reagent were obtained.

(iii) Detection of LAMP Method

To each of the reaction containers prepared in the steps (ii) and (iii) was added a buffer (20 mM Tris-HCl (pH 8.8), 10 mM potassium chloride, 10 mM ammonium sulfate, 8 mM magnesium sulfate, 0.1% Tween 20) to prepare a LAMP reaction solution. Further, M13mp18DNA was added thereto to 100 copies/tube (positive control), whereas a negative control was the LAMP reaction solution to which M13mp18DNA was not added. The reaction solutions were inverted to mix the contents well. After spinning down, a LAMP reaction was performed at 63° C. for 60 minutes.

In all the reaction containers, only the positive control became colored, and thus the target gene was detectable.

Example 15

Change in Absorbance Over Time in LAMP Reaction (Real Time Measurement)

Using quartz cells (optical path length: 1 cm) as reaction containers, LAMP reaction mixtures were prepared as follows. An amount of 50 µl of Reaction Mix, 10 µl of Primer Mix, 4 µl of Bst DNA Polymerase, 1 µl of pyrophosphatase, 30 µl of distilled water, and 4 µl of a nucleic acid detecting reagent (0.1% gentian violet B, 2.1% sodium sulfite, 1.5% β-cyclodextrin) were charged into each of the quartz cells, and stirred well. Further, 1 µl of Positive Control DNA (positive control) or 1 µl of distilled water (negative control) was added to the cell to give a total of 100 µl. The quartz cells were heated at 63° C. for 60 minutes. During the heating, the absorbance at 590 nm was measured over time. Also, the same measurement was performed on a mixture of distilled water and the detecting reagent to obtain the background value.

Figure 14:
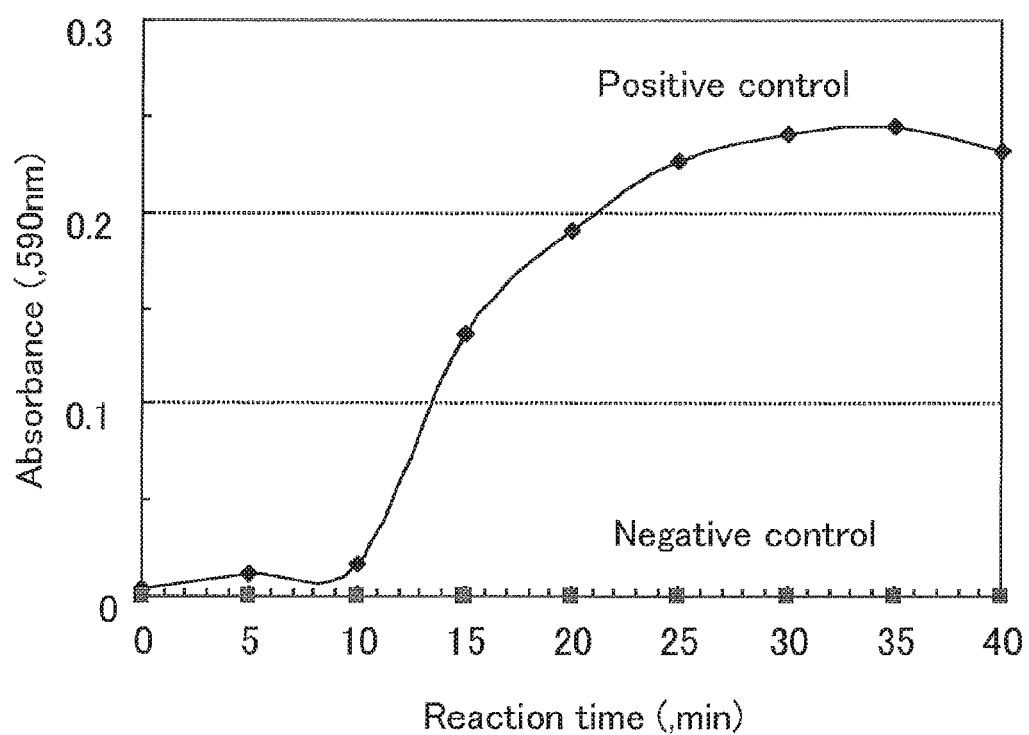
FIG. 14 illustrates time-dependent changes in the absorbance at a wavelength of 590 nm of a LAMP reaction mixture with a detecting reagent.

FIG. 14 shows the measured results minus the background value. This demonstrates that no change in absorbance was observed in the negative control, whereas in the positive control the absorbance began to increase after about 10 minutes and reached a plateau after about 25 minutes. The results show that the nucleic acid amplification by the LAMP reaction was monitorable by observing the absorbance of the present detecting reagent over time.

REFERENCE SIGNS LIST

1 Bottom
2 Body
3 Opening
4 Detecting reagent carrier
5 Wall

The invention claimed is:

1. A method of detecting a single-stranded or multi-stranded nucleic acid, comprising the steps of:
    contacting a single-stranded or multi-stranded nucleic acid with a detecting reagent containing a leuco dye; wherein the leuco dye is initially colorless, and wherein the nucleic acid reacts as a color developer with the colorless leuco dye to change the structure of the colorless leuco dye and produce a colored dye; and
    measuring an absorbance of at least one of the single-stranded or multi-stranded nucleic acid and the detecting reagent under visible light.

2. The method of detecting a nucleic acid according to claim 1, further comprising, prior to or after the contacting step,
    a step of amplifying the nucleic acid.

3. The method of detecting a nucleic acid according to claim 2, wherein amplifying the nucleic acid and measuring the absorbance are performed in a consistently-closed system.

4. The method of detecting a nucleic acid according to claim 2, wherein the absorbance is monitored in real-time.

5. The method of detecting a nucleic acid according to claim 2,
    wherein the nucleic acid is amplified by LAMP method.

6. The method of detecting a nucleic acid according to claim 5,
    wherein a pyrophosphatase is used in the LAMP method.

7. The method of detecting a nucleic acid according to claim 6,
    wherein the pyrophosphatase is a heat resistant pyrophosphatase.

8. The method of detecting a nucleic acid according to claim 1, wherein the detecting reagent is in a solid form.

9. The method of detecting a nucleic acid according to claim 1, wherein the leuco dye is a triarylmethane dye.

10. The method of detecting a nucleic acid according to claim 9, wherein the triarylmethane dye is crystal violet or gentian violet.

11. The method of detecting a nucleic acid according to claim 1
    wherein the detecting reagent contains at least one of a nucleophilic agent and a stabilizer that stabilizes the leuco dye.

12. The method of detecting a nucleic acid according to claim 11,
    wherein the nucleophilic agent is one or more nucleophilic agents selected from the group consisting of sodium borohydride, sodium cyanoborohydride, sodium bisulfite, sodium sulfite, sodium hydrosulfite, potassium pyrosulfite, sodium thiosulfate, glutathione, ascorbic acid, 2-mercaptoethanol, DL-dithiothreitol, 1-thioglycerol, cysteine, tributylphosphine, aminoethanethiol, and tris(2-carboxyethyl)phosphine.

13. The method of detecting a nucleic acid according to claim 11,
    wherein the stabilizer is one or more stabilizers selected from the group consisting of α-cyclodextrin, β-cyclodextrin, γ-cyclodextrin, and ascorbic acid.

\* \* \* \* \*